United States Patent
Nicholas

(10) Patent No.: US 11,877,750 B2
(45) Date of Patent: Jan. 23, 2024

(54) SURGICAL STAPLER WITH POWERED AND MANUAL FUNCTIONS

(71) Applicant: Covidien LP, Mansfield, MA (US)

(72) Inventor: David A. Nicholas, Trumbull, CT (US)

(73) Assignee: Covidien LP, Mansfield, MA (US)

( * ) Notice: Subject to any disclaimer, the term of this patent is extended or adjusted under 35 U.S.C. 154(b) by 38 days.

(21) Appl. No.: 17/543,107

(22) Filed: Dec. 6, 2021

(65) Prior Publication Data

US 2022/0225995 A1 Jul. 21, 2022

Related U.S. Application Data

(60) Provisional application No. 63/140,066, filed on Jan. 21, 2021.

(51) Int. Cl.
| | |
|---|---|
| *A61B 17/115* | (2006.01) |
| *A61B 17/068* | (2006.01) |
| *A61B 90/00* | (2016.01) |
| *A61B 17/34* | (2006.01) |
| *A61B 17/00* | (2006.01) |
| *A61B 17/11* | (2006.01) |

(52) U.S. Cl.
CPC ...... *A61B 17/1155* (2013.01); *A61B 17/3494* (2013.01); *A61B 90/08* (2016.02); *A61B 2017/00115* (2013.01); *A61B 2017/00398* (2013.01); *A61B 2017/1103* (2013.01); *A61B 2090/0811* (2016.02)

(58) Field of Classification Search
CPC .......................... A61B 17/068; A61B 17/1155
See application file for complete search history.

(56) References Cited

U.S. PATENT DOCUMENTS

| | | | |
|---|---|---|---|
| 3,388,847 A | 6/1968 | Kasulin et al. | |
| 3,552,626 A | 1/1971 | Astafiev et al. | |
| 3,638,652 A | 2/1972 | Kelley | |
| 3,771,526 A | 11/1973 | Rudie | |
| 4,198,982 A | 4/1980 | Fortner et al. | |
| 4,207,898 A | 6/1980 | Becht | |
| 4,289,133 A | 9/1981 | Rothfuss | |
| 4,304,236 A | 12/1981 | Conta et al. | |
| 4,319,576 A * | 3/1982 | Rothfuss ............... | A61B 17/115 227/175.3 |
| 4,350,160 A | 9/1982 | Kolesov et al. | |
| 4,351,466 A | 9/1982 | Noiles | |
| 4,379,457 A | 4/1983 | Gravener et al. | |

(Continued)

FOREIGN PATENT DOCUMENTS

| | | |
|---|---|---|
| CA | 908529 A | 8/1972 |
| CA | 2805365 A1 | 8/2013 |

(Continued)

OTHER PUBLICATIONS

Extended European Search Report dated Jan. 11, 2023, issued in corresponding European Appln. No. 22152532, 10 pages.

*Primary Examiner* — Gloria R Weeks
(74) *Attorney, Agent, or Firm* — Carter, DeLuca & Farrell LLP

(57) ABSTRACT

A surgical stapling device for performing anastomoses procedures within a body of a patient includes a handle assembly, an elongate body, and a tool assembly. The handle assembly includes a manually actuated approximation mechanism and a motorized firing mechanism.

20 Claims, 18 Drawing Sheets

(56) References Cited

U.S. PATENT DOCUMENTS

| | | |
|---|---|---|
| 4,473,077 A | 9/1984 | Noiles et al. |
| 4,476,863 A | 10/1984 | Kanshin et al. |
| 4,485,817 A | 12/1984 | Swiggett |
| 4,488,523 A | 12/1984 | Shichman |
| 4,505,272 A | 3/1985 | Utyamyshev et al. |
| 4,505,414 A | 3/1985 | Filipi |
| 4,520,817 A | 6/1985 | Green |
| 4,550,870 A | 11/1985 | Krumme et al. |
| 4,573,468 A | 3/1986 | Conta et al. |
| 4,576,167 A | 3/1986 | Noiles |
| 4,592,354 A | 6/1986 | Rothfuss |
| 4,603,693 A | 8/1986 | Conta et al. |
| 4,606,343 A | 8/1986 | Conta et al. |
| 4,632,290 A | 12/1986 | Green et al. |
| 4,646,745 A | 3/1987 | Noiles |
| 4,665,917 A | 5/1987 | Clanton et al. |
| 4,667,673 A | 5/1987 | Li |
| 4,671,445 A | 6/1987 | Barker et al. |
| 4,700,703 A | 10/1987 | Resnick et al. |
| 4,703,887 A | 11/1987 | Clanton et al. |
| 4,708,141 A | 11/1987 | Inoue et al. |
| 4,717,063 A | 1/1988 | Ebihara |
| 4,752,024 A | 6/1988 | Green et al. |
| 4,754,909 A | 7/1988 | Barker et al. |
| 4,776,506 A | 10/1988 | Green |
| 4,817,847 A | 4/1989 | Redtenbacher et al. |
| 4,873,977 A | 10/1989 | Avant et al. |
| 4,893,662 A | 1/1990 | Gervasi |
| 4,903,697 A | 2/1990 | Resnick et al. |
| 4,907,591 A | 3/1990 | Vasconcellos et al. |
| 4,917,114 A | 4/1990 | Green et al. |
| 4,957,499 A | 9/1990 | Lipatov et al. |
| 4,962,877 A | 10/1990 | Hervas |
| 5,005,749 A | 4/1991 | Aranyi |
| 5,042,707 A | 8/1991 | Taheri |
| 5,047,039 A | 9/1991 | Avant et al. |
| 5,104,025 A | 4/1992 | Main et al. |
| 5,119,983 A | 6/1992 | Green et al. |
| 5,122,156 A | 6/1992 | Granger et al. |
| 5,139,513 A | 8/1992 | Segato |
| 5,158,222 A | 10/1992 | Green et al. |
| 5,188,638 A | 2/1993 | Tzakis |
| 5,193,731 A | 3/1993 | Aranyi |
| 5,197,648 A | 3/1993 | Gingold |
| 5,197,649 A | 3/1993 | Bessler et al. |
| 5,205,459 A | 4/1993 | Brinkerhoff et al. |
| 5,221,036 A | 6/1993 | Takase |
| 5,222,963 A | 6/1993 | Brinkerhoff et al. |
| 5,253,793 A | 10/1993 | Green et al. |
| 5,261,920 A | 11/1993 | Main et al. |
| 5,271,543 A | 12/1993 | Grant et al. |
| 5,271,544 A | 12/1993 | Fox et al. |
| 5,275,322 A | 1/1994 | Brinkerhoff et al. |
| 5,282,810 A | 2/1994 | Allen et al. |
| 5,285,944 A | 2/1994 | Green et al. |
| 5,285,945 A | 2/1994 | Brinkerhoff et al. |
| 5,292,053 A | 3/1994 | Bilotti et al. |
| 5,309,927 A | 5/1994 | Welch |
| 5,312,024 A | 5/1994 | Grant et al. |
| 5,314,435 A | 5/1994 | Green et al. |
| 5,314,436 A | 5/1994 | Wilk |
| 5,330,486 A | 7/1994 | Wilk |
| 5,333,773 A | 8/1994 | Main et al. |
| 5,344,059 A | 9/1994 | Green et al. |
| 5,346,115 A | 9/1994 | Perouse et al. |
| 5,348,259 A | 9/1994 | Blanco et al. |
| 5,350,104 A | 9/1994 | Main et al. |
| 5,355,897 A | 10/1994 | Pietrafitta et al. |
| 5,360,154 A | 11/1994 | Green |
| 5,368,215 A | 11/1994 | Green et al. |
| 5,392,979 A | 2/1995 | Green et al. |
| 5,395,030 A | 3/1995 | Kuramoto et al. |
| 5,403,333 A | 4/1995 | Kaster et al. |
| 5,404,870 A | 4/1995 | Brinkerhoff et al. |
| 5,411,508 A | 5/1995 | Bessler et al. |
| 5,425,738 A | 6/1995 | Gustafson et al. |
| 5,433,721 A | 7/1995 | Hooven et al. |
| 5,437,684 A | 8/1995 | Calabrese et al. |
| 5,439,156 A | 8/1995 | Grant et al. |
| 5,443,198 A | 8/1995 | Viola et al. |
| 5,447,514 A | 9/1995 | Gerry et al. |
| 5,454,825 A | 10/1995 | Van Leeuwen et al. |
| 5,464,144 A | 11/1995 | Guy et al. |
| 5,464,415 A | 11/1995 | Chen |
| 5,470,006 A | 11/1995 | Rodak |
| 5,474,223 A | 12/1995 | Viola et al. |
| 5,497,934 A | 3/1996 | Brady et al. |
| 5,503,635 A | 4/1996 | Sauer et al. |
| 5,522,534 A | 6/1996 | Viola et al. |
| 5,533,661 A | 7/1996 | Main et al. |
| 5,588,579 A | 12/1996 | Schnut et al. |
| 5,609,285 A | 3/1997 | Grant et al. |
| 5,626,591 A | 5/1997 | Kockerling et al. |
| 5,632,433 A | 5/1997 | Grant et al. |
| 5,639,008 A | 6/1997 | Gallagher et al. |
| 5,641,111 A | 6/1997 | Ahrens et al. |
| 5,658,300 A | 8/1997 | Bito et al. |
| 5,669,918 A | 9/1997 | Balazs et al. |
| 5,685,474 A * | 11/1997 | Seeber ............... A61B 17/115 |
| | | 227/19 |
| 5,709,335 A | 1/1998 | Heck |
| 5,715,987 A | 2/1998 | Kelley et al. |
| 5,718,360 A | 2/1998 | Green et al. |
| 5,720,755 A | 2/1998 | Dakov |
| 5,732,872 A | 3/1998 | Bolduc et al. |
| 5,749,896 A | 5/1998 | Cook |
| 5,758,814 A | 6/1998 | Gallagher et al. |
| 5,799,857 A | 9/1998 | Robertson et al. |
| 5,814,055 A | 9/1998 | Knodel et al. |
| 5,833,698 A | 11/1998 | Hinchliffe et al. |
| 5,836,503 A | 11/1998 | Ehrenfels et al. |
| 5,839,639 A | 11/1998 | Sauer et al. |
| 5,855,312 A | 1/1999 | Toledano |
| 5,860,581 A | 1/1999 | Robertson et al. |
| 5,868,760 A | 2/1999 | McGuckin, Jr. |
| 5,881,943 A | 3/1999 | Heck et al. |
| 5,915,616 A | 6/1999 | Viola et al. |
| 5,947,363 A | 9/1999 | Bolduc et al. |
| 5,951,576 A | 9/1999 | Wakabayashi |
| 5,957,363 A | 9/1999 | Heck |
| 5,993,468 A | 11/1999 | Rygaard |
| 6,024,748 A | 2/2000 | Manzo et al. |
| 6,050,472 A | 4/2000 | Shibata |
| 6,053,390 A | 4/2000 | Green et al. |
| 6,068,636 A | 5/2000 | Chen |
| 6,083,241 A | 7/2000 | Longo et al. |
| 6,102,271 A | 8/2000 | Longo et al. |
| 6,117,148 A | 9/2000 | Ravo et al. |
| 6,119,913 A | 9/2000 | Adams et al. |
| 6,126,058 A | 10/2000 | Adams et al. |
| 6,142,933 A | 11/2000 | Longo et al. |
| 6,149,667 A | 11/2000 | Hovland et al. |
| 6,176,413 B1 | 1/2001 | Heck et al. |
| 6,179,195 B1 | 1/2001 | Adams et al. |
| 6,193,129 B1 | 2/2001 | Bittner et al. |
| 6,203,553 B1 | 3/2001 | Robertson et al. |
| 6,209,773 B1 | 4/2001 | Bolduc et al. |
| 6,241,140 B1 | 6/2001 | Adams et al. |
| 6,253,984 B1 | 7/2001 | Heck et al. |
| 6,258,107 B1 | 7/2001 | Balazs et al. |
| 6,264,086 B1 | 7/2001 | McGuckin, Jr. |
| 6,269,997 B1 | 8/2001 | Balazs et al. |
| 6,273,897 B1 | 8/2001 | Dalessandro et al. |
| 6,279,809 B1 | 8/2001 | Nicolo |
| 6,302,311 B1 | 10/2001 | Adams et al. |
| 6,338,737 B1 | 1/2002 | Toledano |
| 6,343,731 B1 | 2/2002 | Adams et al. |
| 6,387,105 B1 | 5/2002 | Gifford, III et al. |
| 6,398,795 B1 | 6/2002 | McAlister et al. |
| 6,402,008 B1 | 6/2002 | Lucas |
| 6,439,446 B1 | 8/2002 | Perry et al. |
| 6,443,973 B1 | 9/2002 | Whitman |
| 6,450,390 B2 | 9/2002 | Heck et al. |
| 6,478,210 B2 | 11/2002 | Adams et al. |

(56) References Cited

U.S. PATENT DOCUMENTS

| | | |
|---|---|---|
| 6,488,197 B1 | 12/2002 | Whitman |
| 6,491,201 B1 | 12/2002 | Whitman |
| 6,494,877 B2 | 12/2002 | Odell et al. |
| 6,503,259 B2 | 1/2003 | Huxel et al. |
| 6,517,566 B1 | 2/2003 | Hovland et al. |
| 6,520,398 B2 | 2/2003 | Nicolo |
| 6,533,157 B1 | 3/2003 | Whitman |
| 6,551,334 B2 | 4/2003 | Blatter et al. |
| 6,578,751 B2 | 6/2003 | Hartwick |
| 6,585,144 B2 | 7/2003 | Adams et al. |
| 6,588,643 B2 | 7/2003 | Bolduc et al. |
| 6,592,596 B1 | 7/2003 | Geitz |
| 6,601,749 B2 | 8/2003 | Sullivan et al. |
| 6,605,078 B2 | 8/2003 | Adams |
| 6,605,098 B2 | 8/2003 | Nobis et al. |
| 6,626,921 B2 | 9/2003 | Blatter et al. |
| 6,629,630 B2 | 10/2003 | Adams |
| 6,631,837 B1 | 10/2003 | Heck |
| 6,632,227 B2 | 10/2003 | Adams |
| 6,632,237 B2 | 10/2003 | Ben-David et al. |
| 6,652,542 B2 | 11/2003 | Blatter et al. |
| 6,659,327 B2 | 12/2003 | Heck et al. |
| 6,676,671 B2 | 1/2004 | Robertson et al. |
| 6,681,979 B2 | 1/2004 | Whitman |
| 6,685,079 B2 | 2/2004 | Sharma et al. |
| 6,695,198 B2 | 2/2004 | Adams et al. |
| 6,695,199 B2 | 2/2004 | Whitman |
| 6,698,643 B2 | 3/2004 | Whitman |
| 6,716,222 B2 | 4/2004 | McAlister et al. |
| 6,716,233 B1 | 4/2004 | Whitman |
| 6,726,697 B2 | 4/2004 | Nicholas et al. |
| 6,742,692 B2 | 6/2004 | Hartwick |
| 6,743,244 B2 | 6/2004 | Blatter et al. |
| 6,763,993 B2 | 7/2004 | Bolduc et al. |
| 6,769,590 B2 | 8/2004 | Vresh et al. |
| 6,769,594 B2 | 8/2004 | Orban, III |
| 6,820,791 B2 | 11/2004 | Adams |
| 6,821,282 B2 | 11/2004 | Perry et al. |
| 6,827,246 B2 | 12/2004 | Sullivan et al. |
| 6,840,423 B2 | 1/2005 | Adams et al. |
| 6,843,403 B2 | 1/2005 | Whitman |
| 6,846,308 B2 | 1/2005 | Whitman et al. |
| 6,852,122 B2 | 2/2005 | Rush |
| 6,866,178 B2 | 3/2005 | Adams et al. |
| 6,872,214 B2 | 3/2005 | Sonnenschein et al. |
| 6,874,669 B2 | 4/2005 | Adams et al. |
| 6,884,250 B2 | 4/2005 | Monassevitch et al. |
| 6,905,504 B1 | 6/2005 | Vargas |
| 6,938,814 B2 | 9/2005 | Sharma et al. |
| 6,942,675 B1 | 9/2005 | Vargas |
| 6,945,444 B2 | 9/2005 | Gresham et al. |
| 6,953,138 B1 | 10/2005 | Dworak et al. |
| 6,957,758 B2 | 10/2005 | Aranyi |
| 6,959,851 B2 | 11/2005 | Heinrich |
| 6,978,922 B2 | 12/2005 | Bilotti et al. |
| 6,981,941 B2 | 1/2006 | Whitman et al. |
| 6,981,979 B2 | 1/2006 | Nicolo |
| 7,032,798 B2 | 4/2006 | Whitman et al. |
| 7,059,331 B2 | 6/2006 | Adams et al. |
| 7,059,510 B2 | 6/2006 | Orban, III |
| 7,077,856 B2 | 7/2006 | Whitman |
| 7,080,769 B2 | 7/2006 | Vresh et al. |
| 7,086,267 B2 | 8/2006 | Dworak et al. |
| 7,114,642 B2 | 10/2006 | Whitman |
| 7,118,528 B1 | 10/2006 | Piskun |
| 7,122,044 B2 | 10/2006 | Bolduc et al. |
| 7,128,748 B2 | 10/2006 | Mooradian et al. |
| 7,141,055 B2 | 11/2006 | Abrams et al. |
| 7,168,604 B2 | 1/2007 | Milliman et al. |
| 7,179,267 B2 | 2/2007 | Nolan et al. |
| 7,182,239 B1 | 2/2007 | Myers |
| 7,195,142 B2 | 3/2007 | Orban, III |
| 7,207,168 B2 | 4/2007 | Doepker et al. |
| 7,220,237 B2 | 5/2007 | Gannoe et al. |
| 7,234,624 B2 | 6/2007 | Gresham et al. |
| 7,235,089 B1 | 6/2007 | McGuckin, Jr. |
| RE39,841 E | 9/2007 | Bilotti et al. |
| 7,285,125 B2 | 10/2007 | Viola |
| 7,303,106 B2 | 12/2007 | Milliman et al. |
| 7,303,107 B2 | 12/2007 | Milliman et al. |
| 7,309,341 B2 | 12/2007 | Ortiz et al. |
| 7,322,994 B2 | 1/2008 | Nicholas et al. |
| 7,325,713 B2 | 2/2008 | Aranyi |
| 7,334,718 B2 | 2/2008 | McAlister et al. |
| 7,335,212 B2 | 2/2008 | Edoga et al. |
| 7,364,060 B2 | 4/2008 | Milliman |
| 7,398,908 B2 | 7/2008 | Holsten et al. |
| 7,399,305 B2 | 7/2008 | Csiky et al. |
| 7,401,721 B2 | 7/2008 | Holsten et al. |
| 7,401,722 B2 | 7/2008 | Hur |
| 7,407,075 B2 | 8/2008 | Holsten et al. |
| 7,410,086 B2 | 8/2008 | Ortiz et al. |
| 7,422,137 B2 | 9/2008 | Manzo |
| 7,422,138 B2 | 9/2008 | Bilotti et al. |
| 7,431,191 B2 | 10/2008 | Milliman |
| 7,438,718 B2 | 10/2008 | Milliman et al. |
| 7,455,676 B2 | 11/2008 | Holsten et al. |
| 7,455,682 B2 | 11/2008 | Viola |
| 7,481,347 B2 * | 1/2009 | Roy ............ A61B 17/07207 227/176.1 |
| 7,494,038 B2 | 2/2009 | Milliman |
| 7,506,791 B2 | 3/2009 | Omaits et al. |
| 7,516,877 B2 | 4/2009 | Aranyi |
| 7,527,185 B2 | 5/2009 | Harari et al. |
| 7,537,602 B2 | 5/2009 | Whitman |
| 7,540,839 B2 | 6/2009 | Butler et al. |
| 7,546,939 B2 | 6/2009 | Adams et al. |
| 7,546,940 B2 | 6/2009 | Milliman et al. |
| 7,547,312 B2 | 6/2009 | Bauman et al. |
| 7,556,186 B2 | 7/2009 | Milliman |
| 7,559,451 B2 | 7/2009 | Sharma et al. |
| 7,585,306 B2 | 9/2009 | Abbott et al. |
| 7,588,174 B2 | 9/2009 | Holsten et al. |
| 7,600,663 B2 | 10/2009 | Green |
| 7,611,038 B2 | 11/2009 | Racenet et al. |
| 7,635,385 B2 | 12/2009 | Milliman et al. |
| 7,669,747 B2 | 3/2010 | Weisenburgh, II et al. |
| 7,686,201 B2 | 3/2010 | Csiky |
| 7,694,864 B2 | 4/2010 | Okada et al. |
| 7,699,204 B2 | 4/2010 | Viola |
| 7,708,181 B2 | 5/2010 | Cole et al. |
| 7,717,313 B2 | 5/2010 | Criscuolo et al. |
| 7,721,932 B2 | 5/2010 | Cole et al. |
| 7,726,539 B2 | 6/2010 | Holsten et al. |
| 7,743,958 B2 | 6/2010 | Orban, III |
| 7,744,627 B2 | 6/2010 | Orban, III et al. |
| 7,770,776 B2 | 8/2010 | Chen et al. |
| 7,771,440 B2 | 8/2010 | Ortiz et al. |
| 7,776,060 B2 | 8/2010 | Mooradian et al. |
| 7,793,813 B2 | 9/2010 | Bettuchi |
| 7,802,712 B2 | 9/2010 | Milliman et al. |
| 7,823,592 B2 | 11/2010 | Bettuchi et al. |
| 7,837,079 B2 | 11/2010 | Holsten et al. |
| 7,837,080 B2 | 11/2010 | Schwemberger |
| 7,837,081 B2 | 11/2010 | Holsten et al. |
| 7,845,536 B2 | 12/2010 | Viola et al. |
| 7,845,538 B2 | 12/2010 | Whitman |
| 7,857,187 B2 | 12/2010 | Milliman |
| 7,886,951 B2 | 2/2011 | Hessler |
| 7,896,215 B2 | 3/2011 | Adams et al. |
| 7,900,806 B2 | 3/2011 | Chen et al. |
| 7,909,039 B2 | 3/2011 | Hur |
| 7,909,219 B2 | 3/2011 | Cole et al. |
| 7,909,222 B2 | 3/2011 | Cole et al. |
| 7,909,223 B2 | 3/2011 | Cole et al. |
| 7,913,892 B2 | 3/2011 | Cole et al. |
| 7,918,377 B2 | 4/2011 | Measamer et al. |
| 7,922,062 B2 | 4/2011 | Cole et al. |
| 7,922,743 B2 | 4/2011 | Heinrich et al. |
| 7,931,183 B2 | 4/2011 | Orban, III |
| 7,938,307 B2 | 5/2011 | Bettuchi |
| 7,942,302 B2 | 5/2011 | Roby et al. |
| 7,951,166 B2 | 5/2011 | Orban, III et al. |
| 7,959,050 B2 | 6/2011 | Smith et al. |

(56) References Cited

U.S. PATENT DOCUMENTS

| | | |
|---|---|---|
| 7,967,181 B2 | 6/2011 | Viola et al. |
| 7,975,895 B2 | 7/2011 | Milliman |
| 8,002,795 B2 | 8/2011 | Beetel |
| 8,006,701 B2 | 8/2011 | Bilotti et al. |
| 8,006,889 B2 | 8/2011 | Adams et al. |
| 3,011,554 A1 | 9/2011 | Milliman |
| 8,011,551 B2 | 9/2011 | Marczyk et al. |
| 8,016,177 B2 | 9/2011 | Bettuchi et al. |
| 8,016,858 B2 | 9/2011 | Whitman |
| 8,020,741 B2 | 9/2011 | Cole et al. |
| 8,025,199 B2 | 9/2011 | Whitman et al. |
| 8,028,885 B2 | 10/2011 | Smith et al. |
| 8,038,046 B2 | 10/2011 | Smith et al. |
| 8,043,207 B2 | 10/2011 | Adams |
| 8,066,167 B2 | 11/2011 | Measamer et al. |
| 8,066,169 B2 | 11/2011 | Viola |
| 8,070,035 B2 | 12/2011 | Holsten et al. |
| 8,070,037 B2 | 12/2011 | Csiky |
| 8,096,458 B2 | 1/2012 | Hessler |
| 8,109,426 B2 | 2/2012 | Milliman et al. |
| 8,109,427 B2 | 2/2012 | Orban, III |
| 8,113,405 B2 | 2/2012 | Milliman |
| 8,113,406 B2 | 2/2012 | Holsten et al. |
| 8,113,407 B2 | 2/2012 | Holsten et al. |
| 8,123,103 B2 | 2/2012 | Milliman |
| 8,128,645 B2 | 3/2012 | Sonnenschein et al. |
| 8,132,703 B2 | 3/2012 | Milliman et al. |
| 8,136,712 B2 | 3/2012 | Zingman |
| 8,146,790 B2 | 4/2012 | Milliman |
| 8,146,791 B2 | 4/2012 | Bettuchi et al. |
| 8,181,838 B2 | 5/2012 | Milliman et al. |
| 8,192,460 B2 | 6/2012 | Orban, III et al. |
| 8,201,720 B2 | 6/2012 | Hessler |
| 8,203,782 B2 | 6/2012 | Brueck et al. |
| 8,211,130 B2 | 7/2012 | Viola |
| 8,225,799 B2 | 7/2012 | Bettuchi |
| 8,225,981 B2 | 7/2012 | Criscuolo et al. |
| 8,231,041 B2 | 7/2012 | Marczyk et al. |
| 8,231,042 B2 | 7/2012 | Hessler et al. |
| 8,257,391 B2 | 9/2012 | Orban, III et al. |
| 8,267,301 B2 | 9/2012 | Milliman et al. |
| 8,272,552 B2 | 9/2012 | Holsten et al. |
| 8,276,802 B2 | 10/2012 | Kostrzewski |
| 8,281,975 B2 | 10/2012 | Criscuolo et al. |
| 8,286,845 B2 | 10/2012 | Perry et al. |
| 8,308,045 B2 | 11/2012 | Bettuchi et al. |
| 8,312,885 B2 | 11/2012 | Bettuchi et al. |
| 8,313,014 B2 | 11/2012 | Bettuchi |
| 8,317,073 B2 | 11/2012 | Milliman et al. |
| 8,317,074 B2 | 11/2012 | Ortiz et al. |
| 8,322,590 B2 | 12/2012 | Patel et al. |
| 8,328,060 B2 | 12/2012 | Jankowski et al. |
| 8,328,062 B2 | 12/2012 | Viola |
| 8,328,063 B2 | 12/2012 | Milliman et al. |
| 8,343,185 B2 | 1/2013 | Milliman et al. |
| 8,353,438 B2 | 1/2013 | Baxter, III et al. |
| 8,353,439 B2 | 1/2013 | Baxter, III et al. |
| 8,353,930 B2 | 1/2013 | Heinrich et al. |
| 8,360,295 B2 | 1/2013 | Milliman et al. |
| 8,360,296 B2 * | 1/2013 | Zingman .............. A61B 17/072 227/176.1 |
| 8,365,974 B2 | 2/2013 | Milliman |
| 8,403,942 B2 | 3/2013 | Milliman et al. |
| 8,408,441 B2 | 4/2013 | Wenchell et al. |
| 8,413,870 B2 | 4/2013 | Pastorelli et al. |
| 8,413,872 B2 | 4/2013 | Patel |
| 8,418,905 B2 | 4/2013 | Milliman |
| 8,418,909 B2 | 4/2013 | Kostrzewski |
| 8,424,535 B2 | 4/2013 | Hessler et al. |
| 8,424,741 B2 | 4/2013 | McGuckin, Jr. et al. |
| 8,430,291 B2 | 4/2013 | Heinrich et al. |
| 8,430,292 B2 | 4/2013 | Patel et al. |
| 8,453,910 B2 | 6/2013 | Bettuchi et al. |
| 8,453,911 B2 | 6/2013 | Milliman et al. |
| 8,479,968 B2 | 7/2013 | Hodgkinson et al. |
| 8,485,414 B2 | 7/2013 | Criscuolo et al. |
| 8,490,853 B2 | 7/2013 | Criscuolo et al. |
| 8,511,533 B2 | 8/2013 | Viola et al. |
| 8,551,138 B2 | 10/2013 | Orban, III et al. |
| 8,567,655 B2 | 10/2013 | Nalagatla et al. |
| 8,579,178 B2 | 11/2013 | Holsten et al. |
| 8,590,763 B2 | 11/2013 | Milliman |
| 8,590,764 B2 | 11/2013 | Hartwick et al. |
| 8,608,047 B2 | 12/2013 | Holsten et al. |
| 8,616,428 B2 | 12/2013 | Milliman et al. |
| 8,616,429 B2 | 12/2013 | Viola |
| 8,622,275 B2 | 1/2014 | Baxter, III et al. |
| 8,627,995 B2 | 1/2014 | Smith et al. |
| 8,631,993 B2 | 1/2014 | Kostrzewski |
| 8,636,187 B2 | 1/2014 | Hueil et al. |
| 8,640,940 B2 | 2/2014 | Ohdaira |
| 8,646,674 B2 | 2/2014 | Schulte et al. |
| 8,662,370 B2 | 3/2014 | Takei |
| 8,663,258 B2 | 3/2014 | Bettuchi et al. |
| 8,672,207 B2 | 3/2014 | Shelton, IV et al. |
| 8,672,931 B2 | 3/2014 | Goldboss et al. |
| 8,672,951 B2 | 3/2014 | Smith et al. |
| 8,678,264 B2 | 3/2014 | Racenet et al. |
| 8,679,137 B2 | 3/2014 | Bauman et al. |
| 8,684,248 B2 | 4/2014 | Milliman |
| 8,684,250 B2 | 4/2014 | Bettuchi et al. |
| 8,684,251 B2 | 4/2014 | Rebuffat et al. |
| 8,684,252 B2 | 4/2014 | Patel et al. |
| 8,695,864 B1 | 4/2014 | Hausen |
| 8,708,212 B2 | 4/2014 | Williams |
| 8,733,611 B2 | 5/2014 | Milliman |
| 8,733,615 B2 | 5/2014 | Nalagatla et al. |
| 8,746,531 B2 | 6/2014 | Wenchell et al. |
| 8,746,532 B2 | 6/2014 | Nalagatla et al. |
| 8,783,543 B2 * | 7/2014 | Shelton, IV ........ G07F 17/3255 227/180.1 |
| 8,789,737 B2 | 7/2014 | Hodgkinson et al. |
| 8,800,838 B2 | 8/2014 | Shelton, IV |
| 8,800,841 B2 | 8/2014 | Ellerhorst et al. |
| 8,801,734 B2 | 8/2014 | Shelton, IV et al. |
| 8,801,735 B2 | 8/2014 | Shelton, IV et al. |
| 8,821,523 B2 | 9/2014 | Heinrich et al. |
| 8,827,903 B2 | 9/2014 | Shelton, IV et al. |
| 8,833,629 B2 | 9/2014 | Nalagatla et al. |
| 8,840,004 B2 | 9/2014 | Holsten et al. |
| 8,844,792 B2 | 9/2014 | Viola |
| 8,845,661 B2 | 9/2014 | D'Arcangelo et al. |
| 8,870,911 B2 | 10/2014 | Williams et al. |
| 8,875,974 B2 | 11/2014 | Rebuffat et al. |
| 8,893,948 B2 | 11/2014 | Williams |
| 8,910,847 B2 | 12/2014 | Nalagatla et al. |
| 8,925,785 B2 | 1/2015 | Holsten et al. |
| 8,925,786 B2 | 1/2015 | Holsten et al. |
| 8,967,448 B2 | 3/2015 | Carter et al. |
| 8,978,955 B2 | 3/2015 | Aronhalt et al. |
| 9,010,608 B2 | 4/2015 | Casasanta, Jr. et al. |
| 9,010,612 B2 | 4/2015 | Stevenson et al. |
| 9,016,540 B2 | 4/2015 | Whitman et al. |
| 9,033,204 B2 | 5/2015 | Shelton, IV et al. |
| 9,095,340 B2 | 8/2015 | Felder et al. |
| 9,113,871 B2 | 8/2015 | Milliman et al. |
| 9,113,877 B1 | 8/2015 | Whitman et al. |
| 9,113,883 B2 | 8/2015 | Aronhalt et al. |
| 9,113,884 B2 | 8/2015 | Shelton, IV et al. |
| 9,113,885 B2 | 8/2015 | Hodgkinson et al. |
| 9,125,654 B2 | 9/2015 | Aronhalt et al. |
| 9,155,536 B1 | 10/2015 | Hausen et al. |
| 9,161,757 B2 | 10/2015 | Bettuchi |
| 9,204,877 B2 * | 12/2015 | Whitman .............. A61B 17/068 |
| 9,204,881 B2 | 12/2015 | Penna |
| 9,211,122 B2 | 12/2015 | Hagerty et al. |
| 9,220,504 B2 | 12/2015 | Viola et al. |
| 9,232,941 B2 | 1/2016 | Mandakolathur Vasudevan et al. |
| 9,232,945 B2 * | 1/2016 | Zingman .......... A61B 17/07207 |
| 9,289,207 B2 | 3/2016 | Shelton, IV |
| 9,301,763 B2 | 4/2016 | Qiao et al. |
| 9,307,994 B2 | 4/2016 | Gresham et al. |
| 9,326,773 B2 | 5/2016 | Casasanta, Jr. et al. |
| 9,351,729 B2 | 5/2016 | Orban, III et al. |

(56) References Cited

U.S. PATENT DOCUMENTS

| | | |
|---|---|---|
| 9,351,731 B2 | 5/2016 | Carter et al. |
| 9,364,229 B2 | 6/2016 | D'Agostino et al. |
| 9,370,366 B2 | 6/2016 | Mozdzierz |
| 9,370,367 B2 | 6/2016 | Mozdzierz |
| 9,393,014 B2 | 7/2016 | Milliman |
| 9,408,603 B2 | 8/2016 | Patel |
| 9,421,013 B2 | 8/2016 | Patel et al. |
| 9,445,817 B2 | 9/2016 | Bettuchi |
| 9,451,962 B2 | 9/2016 | Olson |
| 9,456,821 B2 | 10/2016 | Bettuchi et al. |
| 9,463,022 B2 * | 10/2016 | Swayze .............. A61B 17/1155 |
| 9,492,166 B2 | 11/2016 | Kostrzewski |
| 9,498,222 B2 | 11/2016 | Scheib et al. |
| 9,504,470 B2 | 11/2016 | Milliman |
| 9,522,005 B2 | 12/2016 | Williams et al. |
| 9,532,783 B2 * | 1/2017 | Swayze .............. A61B 17/1155 |
| 9,549,738 B2 | 1/2017 | Mandakolathur Vasudevan et al. |
| 9,572,572 B2 | 2/2017 | Williams |
| 9,579,102 B2 | 2/2017 | Holsten et al. |
| 9,592,055 B2 | 3/2017 | Milliman et al. |
| 9,592,056 B2 | 3/2017 | Mozdzierz et al. |
| 9,597,081 B2 * | 3/2017 | Swayze .............. A61B 17/1155 |
| 9,597,082 B2 | 3/2017 | Stokes et al. |
| 9,603,599 B2 | 3/2017 | Miller et al. |
| 9,629,624 B2 | 4/2017 | Hessler et al. |
| 9,629,633 B2 * | 4/2017 | Williams ............. A61B 17/072 |
| 9,636,112 B2 | 5/2017 | Penna et al. |
| 9,649,110 B2 | 5/2017 | Parihar et al. |
| 9,649,113 B2 | 5/2017 | Ma et al. |
| 9,668,740 B2 | 6/2017 | Williams |
| 9,675,348 B2 | 6/2017 | Smith et al. |
| 9,681,872 B2 | 6/2017 | Jankowski et al. |
| 9,681,873 B2 | 6/2017 | Smith et al. |
| 9,687,234 B2 | 6/2017 | Smith et al. |
| 9,693,773 B2 | 7/2017 | Williams |
| 9,700,309 B2 | 7/2017 | Jaworek |
| 9,706,999 B2 | 7/2017 | Motai |
| 9,713,469 B2 | 7/2017 | Leimbach et al. |
| 9,737,304 B2 | 8/2017 | Bettuchi et al. |
| 9,743,955 B2 | 8/2017 | Hill et al. |
| 9,750,503 B2 | 9/2017 | Milliman |
| 9,763,663 B2 | 9/2017 | Weisshaupt et al. |
| 9,801,626 B2 | 10/2017 | Parihar et al. |
| 9,833,235 B2 | 12/2017 | Penna et al. |
| 9,844,368 B2 | 12/2017 | Boudreaux et al. |
| 9,861,368 B2 | 1/2018 | Racenet et al. |
| 9,883,862 B2 | 2/2018 | Rebuffat et al. |
| 9,907,600 B2 | 3/2018 | Stulen et al. |
| 10,039,549 B2 | 8/2018 | Williams |
| 10,085,744 B2 | 10/2018 | Williams et al. |
| 10,105,137 B2 | 10/2018 | Holsten et al. |
| 10,117,655 B2 | 11/2018 | Scirica et al. |
| 10,117,656 B2 | 11/2018 | Sgroi, Jr. |
| 10,136,888 B2 | 11/2018 | Chen et al. |
| 10,149,680 B2 | 12/2018 | Parihar et al. |
| 10,154,845 B2 | 12/2018 | Williams |
| 10,172,622 B2 | 1/2019 | Kelley |
| 10,178,994 B2 | 1/2019 | Lee et al. |
| 10,188,386 B2 | 1/2019 | Measamer et al. |
| 10,190,888 B2 | 1/2019 | Hryb et al. |
| 10,194,911 B2 | 2/2019 | Miller et al. |
| 10,226,253 B2 * | 3/2019 | DiNardo .............. A61B 17/068 |
| 10,245,038 B2 | 4/2019 | Hopkins et al. |
| 10,271,842 B2 | 4/2019 | Fox et al. |
| 10,271,843 B2 | 4/2019 | Shi et al. |
| 10,307,157 B2 | 6/2019 | Miller et al. |
| 10,321,908 B2 | 6/2019 | Carter et al. |
| 10,327,779 B2 | 6/2019 | Richard et al. |
| 10,342,629 B2 | 7/2019 | Penna et al. |
| 10,405,855 B2 | 9/2019 | Stager et al. |
| 10,413,299 B2 | 9/2019 | Milliman |
| 10,426,468 B2 | 10/2019 | Contini et al. |
| 10,426,480 B2 | 10/2019 | Scirica et al. |
| 10,433,848 B2 | 10/2019 | Chen et al. |
| 10,456,134 B2 | 10/2019 | DiNardo et al. |
| 10,463,365 B2 | 11/2019 | Williams |
| 10,463,373 B2 | 11/2019 | Mozdzierz et al. |
| 10,463,374 B2 | 11/2019 | Sgroi, Jr. |
| 10,470,770 B2 | 11/2019 | Shelton, IV et al. |
| 10,470,771 B2 | 11/2019 | D'Agostino et al. |
| 10,499,922 B2 | 12/2019 | Sgroi, Jr. |
| 10,506,920 B2 | 12/2019 | Hasser et al. |
| 10,507,039 B2 | 12/2019 | Williams |
| 10,512,467 B2 | 12/2019 | Swayze et al. |
| 10,524,795 B2 | 1/2020 | Nalagatla et al. |
| 10,524,798 B2 | 1/2020 | Williams |
| 10,524,868 B2 | 1/2020 | Cooper et al. |
| 10,537,331 B2 | 1/2020 | Scirica et al. |
| 10,542,993 B2 | 1/2020 | Guerrera et al. |
| 10,548,597 B2 * | 2/2020 | Dunki-Jacobs ........ A61B 17/26 |
| 10,548,598 B2 | 2/2020 | Prescott et al. |
| 10,561,424 B2 | 2/2020 | Penna et al. |
| 10,568,631 B2 | 2/2020 | Rebuffat et al. |
| 10,575,847 B2 | 3/2020 | Hessler et al. |
| 10,595,871 B2 | 3/2020 | Racenet et al. |
| 10,595,872 B2 | 3/2020 | Milliman |
| 10,603,042 B2 | 3/2020 | Sgroi |
| 10,624,646 B2 | 4/2020 | Bae et al. |
| 10,639,041 B2 | 5/2020 | Williams |
| 10,653,414 B2 | 5/2020 | Williams |
| 10,898,196 B2 | 1/2021 | Sapienza et al. |
| 11,207,067 B2 * | 12/2021 | Shelton, IV ....... A61B 17/0682 |
| 11,373,755 B2 * | 6/2022 | Shelton, IV .............. G06F 3/02 |
| 11,376,001 B2 * | 7/2022 | Shelton, IV ..... A61B 17/00234 |
| 11,471,155 B2 * | 10/2022 | Shelton, IV ........... A61B 34/30 |
| 2003/0111507 A1 | 6/2003 | Nunez |
| 2005/0006433 A1 * | 1/2005 | Milliman ............ A61B 17/1114 |
| | | 227/176.1 |
| 2005/0051597 A1 | 3/2005 | Toledano |
| 2005/0107813 A1 | 5/2005 | Gilete Garcia |
| 2006/0000869 A1 | 1/2006 | Fontayne |
| 2006/0011698 A1 | 1/2006 | Okada et al. |
| 2006/0201989 A1 | 9/2006 | Ojeda |
| 2007/0027473 A1 | 2/2007 | Vresh et al. |
| 2007/0029363 A1 | 2/2007 | Popov |
| 2007/0060952 A1 | 3/2007 | Roby et al. |
| 2008/0308606 A1 * | 12/2008 | Timm .............. A61B 17/07207 |
| | | 227/175.2 |
| 2009/0236392 A1 | 9/2009 | Cole et al. |
| 2009/0236398 A1 | 9/2009 | Cole et al. |
| 2009/0236401 A1 | 9/2009 | Cole et al. |
| 2010/0019016 A1 | 1/2010 | Edoga et al. |
| 2010/0051668 A1 | 3/2010 | Milliman et al. |
| 2010/0084453 A1 | 4/2010 | Hu |
| 2010/0163598 A1 | 7/2010 | Belzer |
| 2010/0224668 A1 | 9/2010 | Fontayne et al. |
| 2010/0230465 A1 | 9/2010 | Smith et al. |
| 2011/0011916 A1 | 1/2011 | Levine |
| 2011/0114697 A1 | 5/2011 | Baxter, III et al. |
| 2011/0114700 A1 | 5/2011 | Baxter, III et al. |
| 2011/0144640 A1 | 6/2011 | Heinrich et al. |
| 2011/0192882 A1 | 8/2011 | Hess et al. |
| 2012/0145755 A1 | 6/2012 | Kahn |
| 2012/0193395 A1 | 8/2012 | Pastorelli et al. |
| 2012/0193398 A1 | 8/2012 | Williams et al. |
| 2012/0232339 A1 | 9/2012 | Csiky |
| 2012/0273548 A1 | 11/2012 | Ma et al. |
| 2013/0020372 A1 | 1/2013 | Jankowski et al. |
| 2013/0020373 A1 | 1/2013 | Smith et al. |
| 2013/0032628 A1 | 2/2013 | Li et al. |
| 2013/0060258 A1 | 3/2013 | Giacomantonio |
| 2013/0105544 A1 | 5/2013 | Mozdzierz et al. |
| 2013/0105551 A1 | 5/2013 | Zingman |
| 2013/0126580 A1 | 5/2013 | Smith et al. |
| 2013/0153631 A1 | 6/2013 | Vasudevan et al. |
| 2013/0175315 A1 | 7/2013 | Milliman |
| 2013/0175318 A1 | 7/2013 | Felder et al. |
| 2013/0181035 A1 | 7/2013 | Milliman |
| 2013/0181036 A1 | 7/2013 | Olson et al. |
| 2013/0193190 A1 | 8/2013 | Carter et al. |
| 2013/0200131 A1 | 8/2013 | Racenet et al. |
| 2013/0206816 A1 | 8/2013 | Penna |
| 2013/0240597 A1 | 9/2013 | Milliman et al. |
| 2013/0277411 A1 | 10/2013 | Hodgkinson et al. |

(56) References Cited

U.S. PATENT DOCUMENTS

| | | |
|---|---|---|
| 2013/0284792 A1 | 10/2013 | Ma |
| 2014/0008413 A1 | 1/2014 | Williams |
| 2014/0046352 A1 | 2/2014 | Reboa et al. |
| 2014/0158747 A1 | 6/2014 | Measamer et al. |
| 2014/0166727 A1* | 6/2014 | Swayze ............... A61B 17/1155 227/175.1 |
| 2014/0284370 A1 | 9/2014 | Sahin |
| 2015/0083772 A1 | 3/2015 | Miller et al. |
| 2015/0173763 A1 | 6/2015 | Liu |
| 2015/0209045 A1 | 7/2015 | Hodgkinson et al. |
| 2016/0374684 A1* | 12/2016 | DiNardo ............... A61B 17/068 227/179.1 |
| 2017/0079648 A1* | 3/2017 | Wang ................... A61B 17/072 |
| 2017/0128068 A1 | 5/2017 | Zhang et al. |
| 2020/0205817 A1* | 7/2020 | Nielsen ............. A61B 17/1155 |
| 2020/0237375 A1* | 7/2020 | Zhang ................ A61B 17/1155 |
| 2020/0337702 A1* | 10/2020 | Shelton, IV ..... A61B 17/07207 |
| 2022/0225995 A1* | 7/2022 | Nicholas ............ A61B 17/1155 |
| 2023/0064821 A1* | 3/2023 | Shelton, IV ....... H03K 17/9535 |

FOREIGN PATENT DOCUMENTS

| | | |
|---|---|---|
| CN | 104039244 A | 9/2014 |
| CN | 104042288 A | 9/2014 |
| CN | 104367360 A | 2/2015 |
| CN | 211911740 U | 11/2020 |
| DE | 1057729 B | 5/1959 |
| DE | 3301713 A1 | 7/1984 |
| EP | 0152382 A2 | 8/1985 |
| EP | 0173451 A1 | 3/1986 |
| EP | 0190022 A2 | 8/1986 |
| EP | 0282157 A1 | 9/1988 |
| EP | 0503689 A2 | 9/1992 |
| EP | 1354560 A2 | 10/2003 |
| EP | 1671597 A1 | 6/2006 |
| EP | 2138118 A2 | 12/2009 |
| EP | 2168510 A1 | 3/2010 |
| EP | 2238926 A2 | 10/2010 |
| EP | 2524656 A2 | 11/2012 |
| EP | 3023077 A1 | 5/2016 |
| EP | 3412225 A1 | 12/2018 |
| EP | 3549545 A2 | 10/2019 |
| EP | 3705061 A2 | 9/2020 |
| FR | 1136020 A | 5/1957 |
| FR | 1461464 A | 2/1966 |
| FR | 1588250 A | 4/1970 |
| FR | 2443239 A1 | 7/1980 |
| GB | 1185292 A | 3/1970 |
| GB | 2016991 A | 9/1979 |
| GB | 2070499 A | 9/1981 |
| JP | 2004147969 A | 5/2004 |
| JP | 2013138860 A | 7/2013 |
| NL | 7711347 A | 4/1979 |
| SU | 1509052 A1 | 9/1989 |
| WO | 8706448 A1 | 11/1987 |
| WO | 8900406 A1 | 1/1989 |
| WO | 9006085 A1 | 6/1990 |
| WO | 9835614 A1 | 8/1998 |
| WO | 0154594 A1 | 8/2001 |
| WO | 02080781 A2 | 10/2002 |
| WO | 2004047654 A2 | 6/2004 |
| WO | 2008107918 A1 | 9/2008 |
| WO | 2017066918 A1 | 4/2017 |
| WO | 2019130087 A1 | 7/2019 |

* cited by examiner

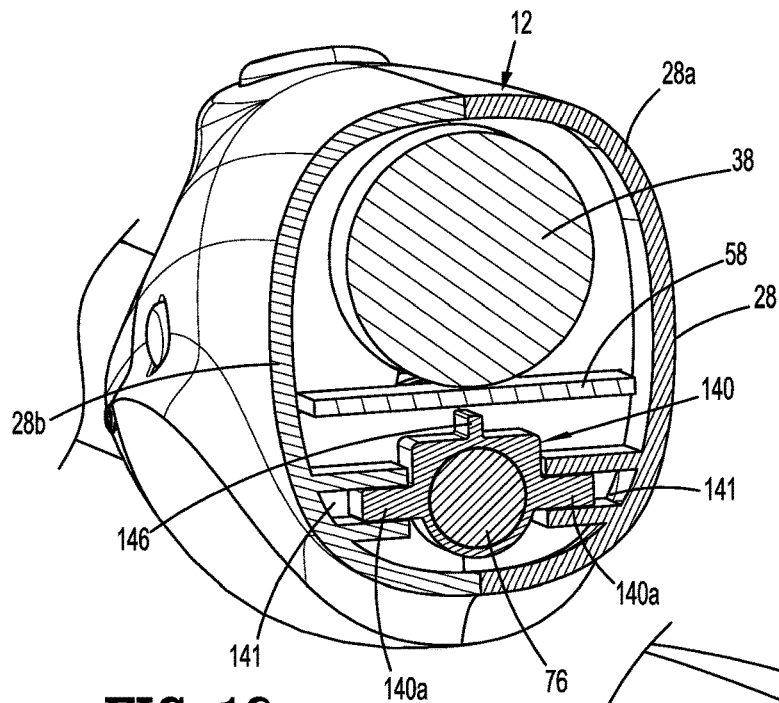
FIG. 16
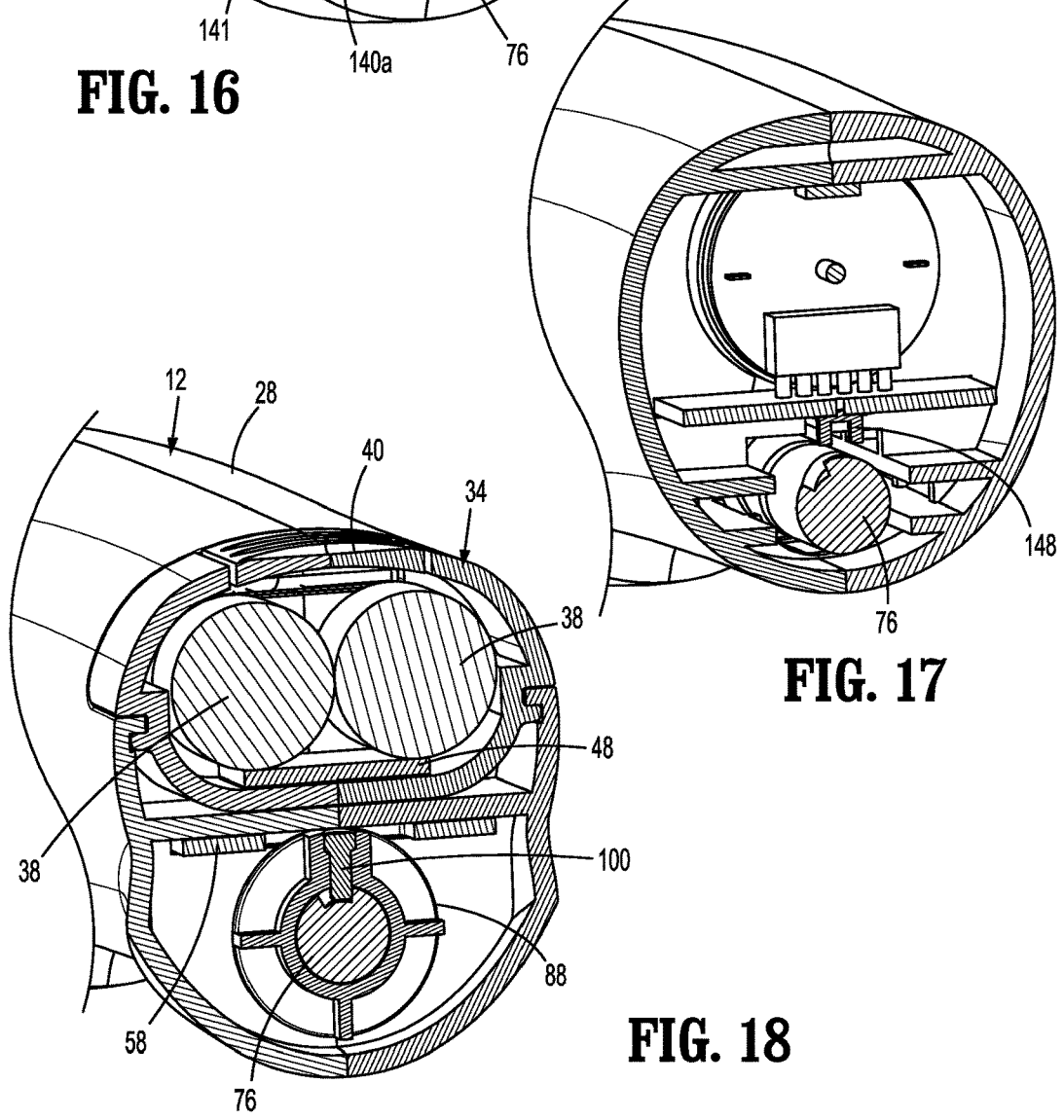
FIG. 17
FIG. 18

SURGICAL STAPLER WITH POWERED AND MANUAL FUNCTIONS

CROSS-REFERENCE TO RELATED APPLICATION

This application claims the benefit of and priority to U.S. Provisional Patent Application No. 63/140,066, filed Jan. 21, 2021, the entire contents each of which is incorporated by reference herein.

FIELD

This disclosure is generally related to surgical stapling devices and, more particularly, to surgical stapling devices for performing anastomoses procedures.

BACKGROUND

Circular stapling devices are used to perform a variety of anastomoses procedures in which two tubular anatomical tissues structures are joined together. These procedures include colorectal circular anastomosis, esophageal circular anastomosis, and bariatric circular anastomosis. Typically, a circular stapling device includes an adapter assembly that connects a tool assembly to a handle assembly. The tool assembly includes an anvil assembly and a shell assembly that are movable in relation to each other in response actuation of an approximation mechanism to clamp tissue between the anvil and shell assemblies. The shell assembly includes a staple cartridge, a staple pusher, and an annular knife. The staple cartridge supports one or more annular rows of staples, and the staple pusher is movable within the staple cartridge in response to actuation of a firing mechanism to eject the staples from the staple cartridge into the anvil assembly. The annular knife is positioned radially inward of the annular rows of staples and is movable from a retracted position to an advanced position to cut or core tissue against the anvil assembly.

Circular stapling devices are available in manual and powered configurations. Typically, the powered configurations include one or more motors located in the handle assembly that drive the approximation and firing mechanisms to actuate the stapling device, and the manual configurations include a rotation knob to actuate the approximation mechanism and a firing trigger to actuate the firing mechanism. Both device configurations have advantages. Due to higher costs of the components, powered stapling devices (or portions thereof) are configured to be reusable, whereas due to the lower costs, manual stapling devices are configured to be disposable. Reusable stapling devices must be properly sterilized.

A continuing need exists for a circular stapling device that has the advantages of both the powered and manual stapling device configurations and is disposable.

SUMMARY

This disclosure generally relates to a surgical stapling device for performing anastomoses procedures within a body of a patient. The surgical stapling device includes a handle assembly that includes a manually actuated approximation mechanism and a motorized firing mechanism.

Aspects of the disclosure are directed to a surgical stapling device that includes a handle assembly, an elongate body, an anvil retainer, and a tool assembly. The elongate body has a distal portion and a proximal portion. The anvil retainer extends from the distal portion of the elongate body. The tool assembly is supported on the distal portion of the elongate body and includes an anvil assembly and a shell assembly. The anvil assembly has an annular staple forming surface and the shell assembly has an annular staple cartridge. The anvil assembly is coupled to the anvil retainer and is movable with the anvil retainer to move the tool assembly between an open position in which the annular staple forming surface of the anvil assembly is spaced from the annular staple cartridge of the shell assembly and a clamped position in which annular staple forming surface of the anvil assembly is in juxtaposed opposition to the annular staple cartridge of the shell assembly. The shell assembly further includes a staple pusher and an annular knife that are movable in relation to the annular staple cartridge between retracted and advanced positions to eject staples from the annular staple cartridge and cut tissue. The handle assembly includes a body portion, a manually operated approximation mechanism, and a motorized firing mechanism. The approximation mechanism is coupled to the anvil retainer and is manually operable to retract the anvil retainer into the shell assembly to move the tool assembly from the open position to the clamped position. The firing mechanism includes a motor that is activated to move the staple pusher and the annular knife between their retracted and advanced positions.

In aspects of the disclosure, the body portion of the handle assembly supports a battery pack that includes one or more batteries that are electrically coupled to the motor by circuitry.

In some aspects of the disclosure, the manually operated approximation mechanism includes a rotation knob, a rotatable sleeve, a drive screw, and a screw extension.

In certain aspects of the disclosure, the rotatable knob is coupled to the drive screw by the rotatable sleeve such that rotation of the rotation knob causes longitudinal movement of the drive screw between advanced and retracted positions.

In aspects of the disclosure, the drive screw is coupled to the anvil retainer by one or more extensions that are formed of a resilient material and extend through the elongate body.

In some aspects of the disclosure, the handle assembly supports a photo interrupter, and the drive screw supports a carriage that has an elongate rib. The carriage is fixedly secured to the drive screw and movable with the drive screw between advanced and retracted positions such that the elongate rib is received within the photo interrupter when the carriage and the drive screw are near their retracted positions.

In certain aspects of the disclosure, the handle assembly includes at least one safety switch that is supported within the body portion of the handle assembly and at least one safety button that is supported on the body portion of the handle assembly.

In aspects of the disclosure, the at least one safety switch is activated when the elongate rib of the carriage is received within the photo interrupter.

In some aspects of the disclosure, the handle assembly includes a fire switch and a fire button. The fire switch is supported within the body portion of the handle assembly and the fire button is supported on the body portion of the handle assembly.

In certain aspects of the disclosure, the fire switch is activated when the at least one safety button is depressed to close the at least one safety switch after the safety switch is activated, and the fire button is depressible to close the fire switch after the fire switch is activated to activate the motor.

In aspects of the disclosure, the at least one safety switch includes first and second safety switches and the at least one safety button includes first and second safety buttons.

In some aspects of the disclosure, the first and second safety buttons are supported on opposite sides of the body portion of the handle assembly.

In certain aspects of the disclosure, the safety button illuminates when the safety switch is activated, and the fire button illuminates when the fire switch is activated.

In aspects of the disclosure, the motorized firing mechanism includes a fire gear, a fire screw, an extender, a pusher link, and a pusher, and the motor includes a drive shaft that supports an output gear.

In some aspects of the disclosure, the fire gear includes an outer gear member that is engaged with the output gear such that activation of the motor causes rotation of the fire gear.

In certain aspects of the disclosure, the fire gear defines an internally threaded bore and the fire screw includes an outer threaded portion. The fire screw is received within the internally threaded bore of the of the fire gear such that rotation of the fire gear causes longitudinal movement of the fire screw between retracted and advanced positions.

In aspects of the disclosure, the fire screw is coupled to the pusher link by the extender and the pusher link is coupled to the pusher such that longitudinal movement of the fire screw causes corresponding longitudinal movement of the pusher link and the pusher.

In some aspects of the disclosure, the approximation knob defines a through bore and has a proximal portion that supports an indicator cap that defines at least one window.

In certain aspects of the disclosure, the stapling device includes an indicator mechanism that includes an indicator, an adjustment member, and a biasing member.

In aspects of the disclosure, the indicator includes indicia and is movable within the through bore of the approximation knob from an advanced position to a retracted position in response to movement of the drive screw from its' advanced position towards its retracted position to position the indicia in a position within the approximation knob to be visualized through the at least one window in the indicator cap.

In some aspects of the disclosure, the adjustment member is threadedly engaged with the indicator and includes a distal portion that extends distally of the indicator and is positioned to engage the drive screw as the drive screw is moved towards its retracted position to move the indicator towards its' retracted position.

In certain aspects of the disclosure, a longitudinal position of the adjustment member in relation to the indicator is adjustable to properly position the adjustment member in relation to the drive screw within the through bore of the approximation knob such that the indicia moves into the at least one window of the indicator cap when the tool assembly is in the clamped position.

Another aspect of the disclosure is directed to a handle assembly that includes a body portion, a manually operated approximation mechanism, and a motorized firing mechanism. The approximation mechanism includes an approximation knob and a drive screw. The approximation knob is rotatable to cause longitudinal movement of the drive screw. The firing mechanism includes a motor and a fire screw. The motor is coupled to the fire screw such that activation of the motor causes longitudinal movement of the drive screw.

In aspects of the disclosure, the motorized firing mechanism further includes a fire gear, and the motor includes an output shaft that supports an output gear. The fire gear includes an outer gear member that is engaged with the output gear such that activation of the motor causes rotation of the fire gear.

In some aspects of the disclosure, the fire gear defines an internally threaded bore and the fire screw includes an outer threaded portion. The fire screw is received within the internally threaded bore of the fire gear such that rotation of the fire gear causes longitudinal movement of the fire screw between retracted and advanced positions.

Another aspect of the disclosure is directed to an approximation knob assembly including an approximation knob, an indicator cap, and an indicator mechanism. The approximation knob defines a through bore and has a proximal portion. The indicator cap is supported on the proximal portion of the approximation knob and defines at least one window. The indicator mechanism includes an indicator, an adjustment member, and a biasing member. The indicator includes indicia and is movable within the through bore of the approximation knob from an advanced position to a retracted position to position the indicia in a position within the approximation knob to be visualized through the at least one window in the indicator cap. The adjustment member is threadedly engaged with the indicator and includes a distal portion that extends distally from the indicator. The longitudinal position of the adjustment member is adjustable in relation to the indicator.

Other aspects, features, and advantages will be apparent from the description, the drawings, and the claims that follow.

BRIEF DESCRIPTION OF DRAWINGS

Various aspects and features of the disclosure are described with reference to the drawings wherein like numerals designate identical or corresponding elements in each of the several views wherein:

FIG. 16 is a cross-sectional view taken along section line 16-16 of FIG. 5;

FIG. 17 is a cross-sectional view taken along section line 17-17 of FIG. 5;

FIG. 18 is a cross-sectional view taken along section line 18-18 of FIG. 5;

DETAILED DESCRIPTION

Figure 1:
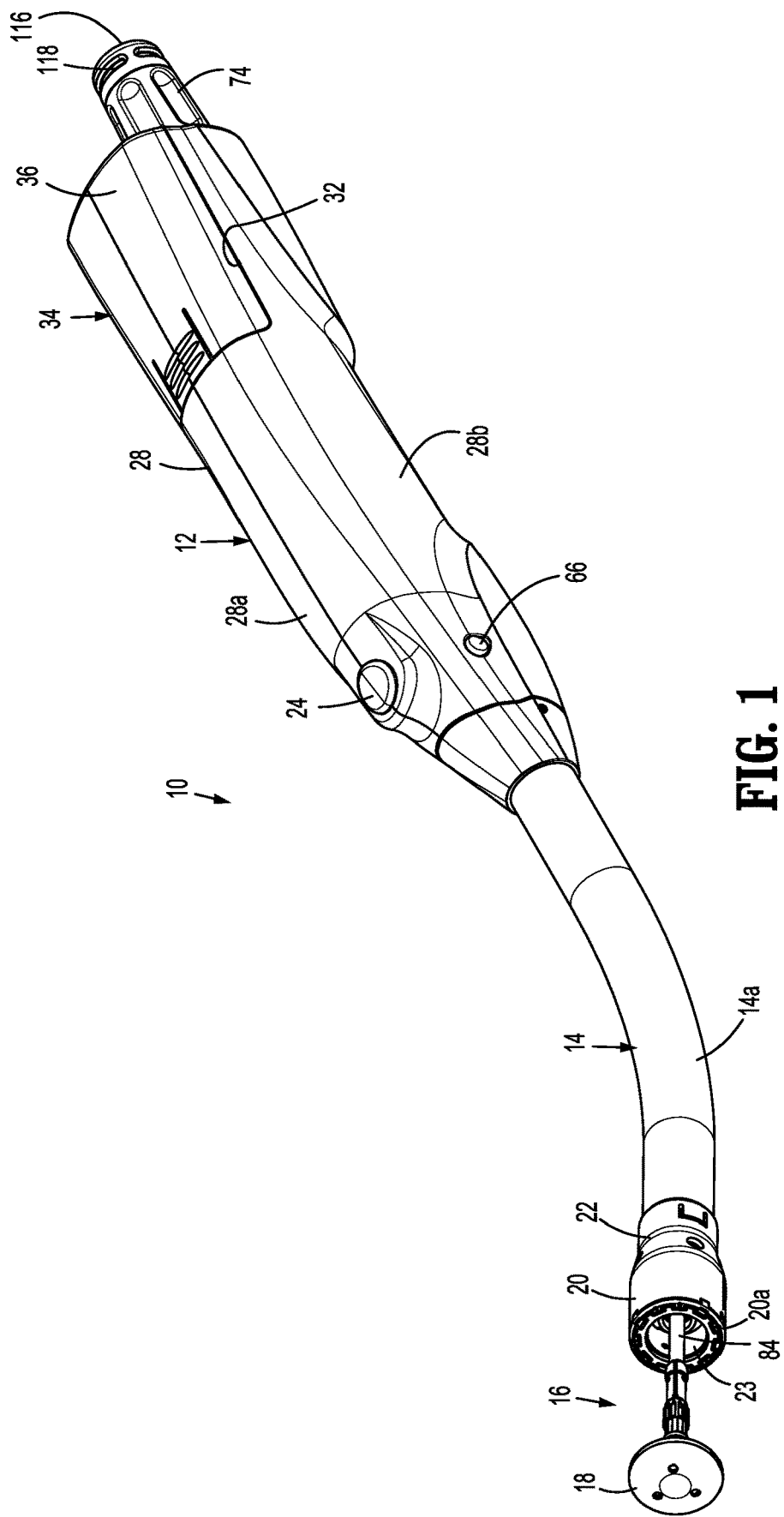
FIG. 1 is a side perspective view of a circular stapling device according to aspects of the disclosure with a tool assembly in an unclamped position.

The disclosed surgical stapling device will now be described in detail with reference to the drawings in which like reference numerals designate identical or corresponding elements in each of the several views. However, it is to be understood that the disclosed aspects are merely exemplary of the disclosure and may be embodied in various forms. Well-known functions or constructions are not described in detail to avoid obscuring the disclosure in unnecessary detail. Therefore, specific structural and functional details disclosed herein are not to be interpreted as limiting, but merely as a basis for the claims and as a representative basis for teaching one skilled in the art to variously employ the disclosure in virtually any appropriately detailed structure.

In this description, the term "proximal" is used generally to refer to that portion of the device that is closer to a clinician during use of the device for its intended purpose, while the term "distal" is used generally to refer to that portion of the device that is farther from the clinician during use of the device for its intended purpose. In addition, the terms "about" and "substantially" are intended to include a range that includes the listed parameter and plus or minus ten percent of the listed parameter. Further, the term "clinician" is used generally to refer to medical personnel including doctors, nurses, and support personnel.

This disclosure is directed to a surgical stapling device for performing anastomoses procedures that includes a motor for driving a firing mechanism and a manually actuated approximation knob for approximating a tool assembly of the stapling device.

Figure 2:
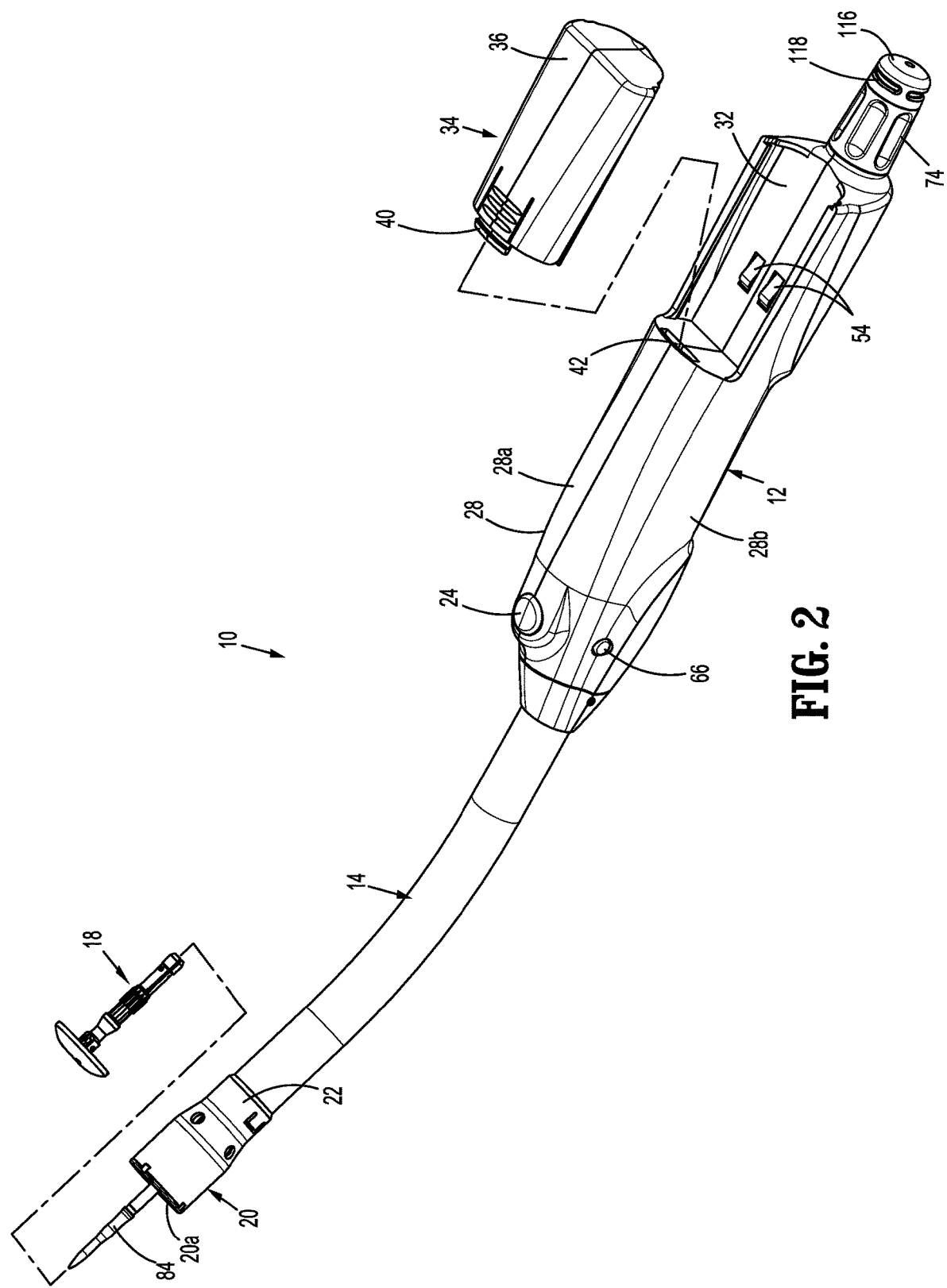
FIG. 2 is a side perspective view of the circular stapling device shown in FIG. 1 with an anvil assembly and a battery pack separated from the stapling device.
Figure 19:
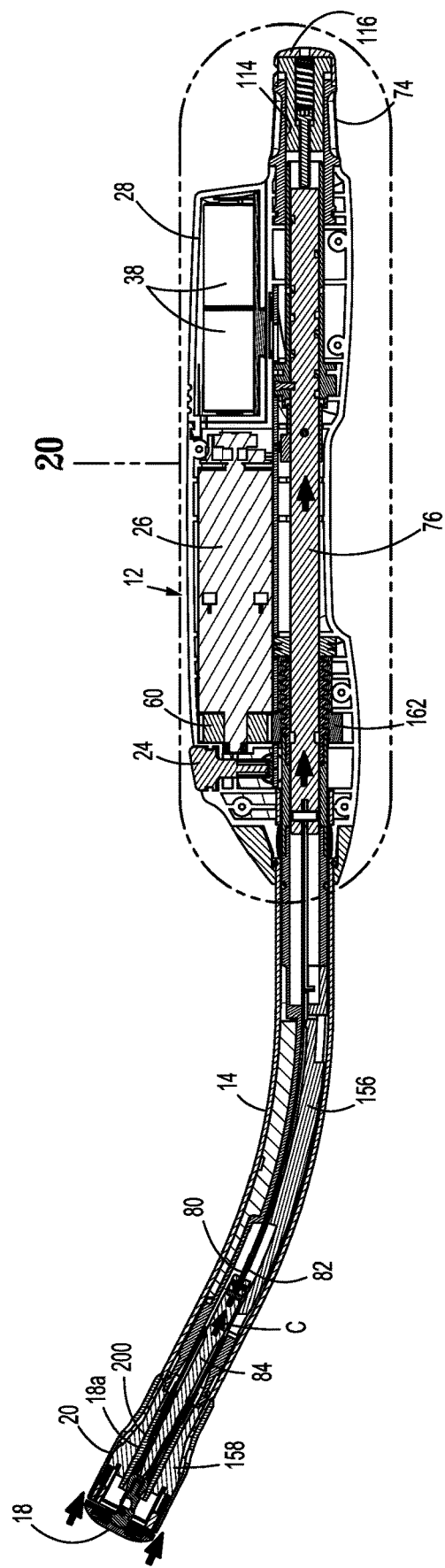
FIG. 19 is a cross-sectional view taken along the longitudinal axis of the circular stapling device shown in FIG. 1 in the clamped position.

FIGS. 1 and 2 illustrate a circular stapling device shown generally as stapling device 10 which includes a handle assembly 12, an elongate body 14, and a tool assembly 16. The tool assembly 16 includes an anvil assembly 18 that has an annular staple forming surface 18a (FIG. 7) and a shell assembly 20 that has an annular staple cartridge 20a (FIG. 1) that supports staples (not shown). The anvil assembly 18 is supported for movement in relation to the shell assembly 20 between an open or unclamped position (FIG. 1) and a clamped position (FIG. 19). In aspects of the disclosure, the shell assembly 20 includes a proximal portion 22 that is coupled to a distal portion of the elongate body 14 and the adapter assembly 20 includes a proximal portion that is coupled to the handle assembly 12. It is envisioned that the shell assembly 20 can be releasably secured to the elongate body 14 and/or the elongate body 14 can be releasably secured to the handle assembly 12. The shell assembly also includes a knife 23 (FIG. 1) that is movable between retracted and advanced positions to cut tissue during an anastomosis procedure.

The circular stapling device 10 includes a hybrid type handle assembly 12 that includes a manually operated approximation knob 74 for approximating the anvil assembly 18 with the shell assembly 20 and a fire button 24 for activating a motor 26 (FIG. 4) for stapling and cutting tissue. The handle assembly 12 includes a body portion 28 that is ergonomically shaped to be gripped by a clinician. The body portion 28 defines an internal cavity 30 (FIG. 4) and an external recess 32 (FIG. 2). The internal cavity 30 receives drive components of the handle assembly described below. The external recess 32 receives a battery pack 34 that is releasably coupled to the body portion 28 of the handle assembly 12. The battery pack 34 includes a housing 36 and one or more batteries 38 that are received within the housing 36. The housing 36 of the battery pack 34 has a distal portion that is formed with a resilient latch 40 that is received in a slot 42 (FIG. 2) formed in the body portion 28. The resilient latch 40 engages the body portion 28 in a snap-fit manner to releasably secure the battery pack 34 to the body portion 28 of the handle assembly 12.

Figure 3:
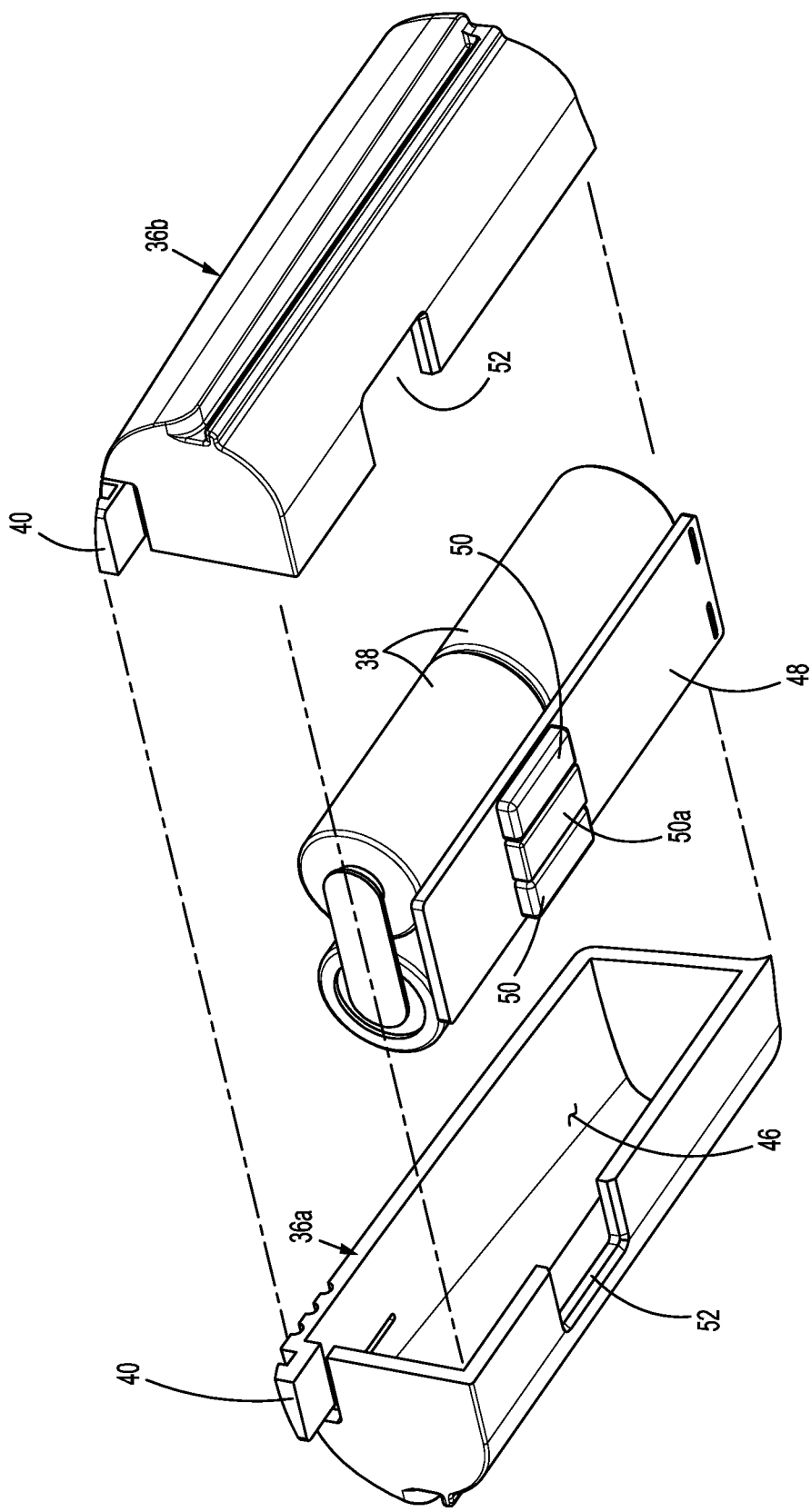
FIG. 3 is an exploded side perspective view of the battery pack of the stapling device shown in FIG. 2.

FIG. 3 illustrates the battery pack 34 of the handle assembly 12. In aspects of the disclosure, the housing 36 of the battery pack 34 is formed from half-sections 36a, 36b that are coupled together to define a cavity 46 that receives the batteries 38. The batteries 38 are supported on a printed circuit board 48 that includes electrical contacts 50. The half-sections 36a, 36b when coupled together define an opening 52 that receives the electrical contact 50 such that the electrical contact 50 can engage contacts within the handle assembly 12 to supply power to the motor 26. The battery contacts may be in the form of spring fingers 54.

Figure 4:
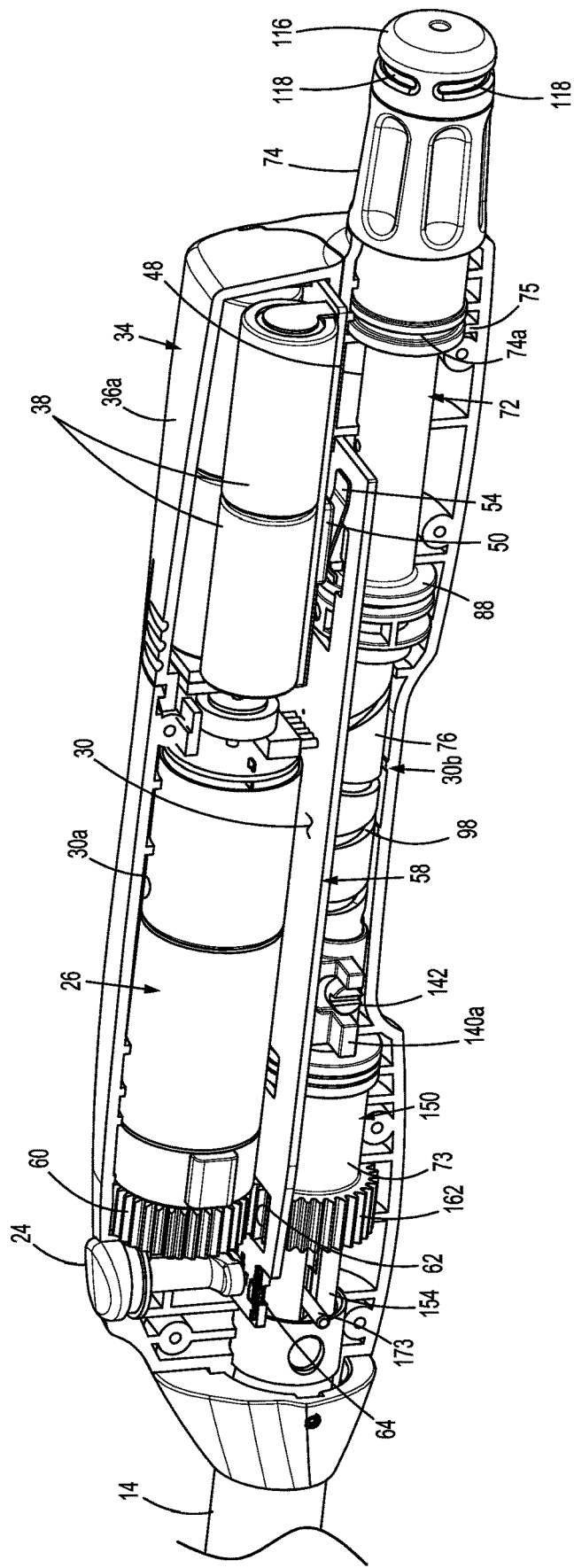
FIG. 4 is a side perspective view from above of the handle assembly shown in FIG. 1 assembled with a body half-section of the handle assembly removed.
Figure 5:
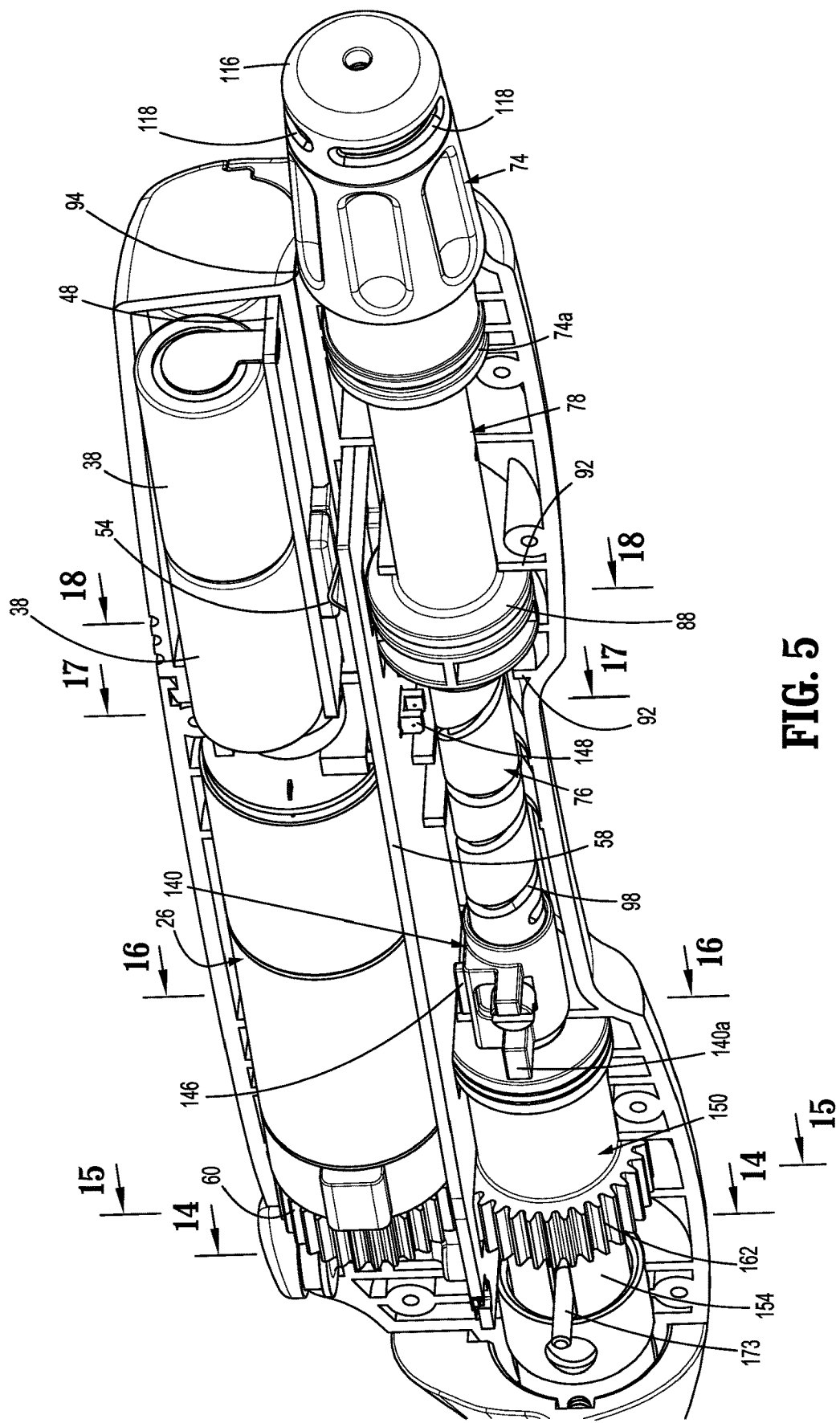
FIG. 5 is a side perspective view from below of the handle assembly shown in FIG. 4 assembled with a body half-section of the handle assembly removed.
Figure 6:
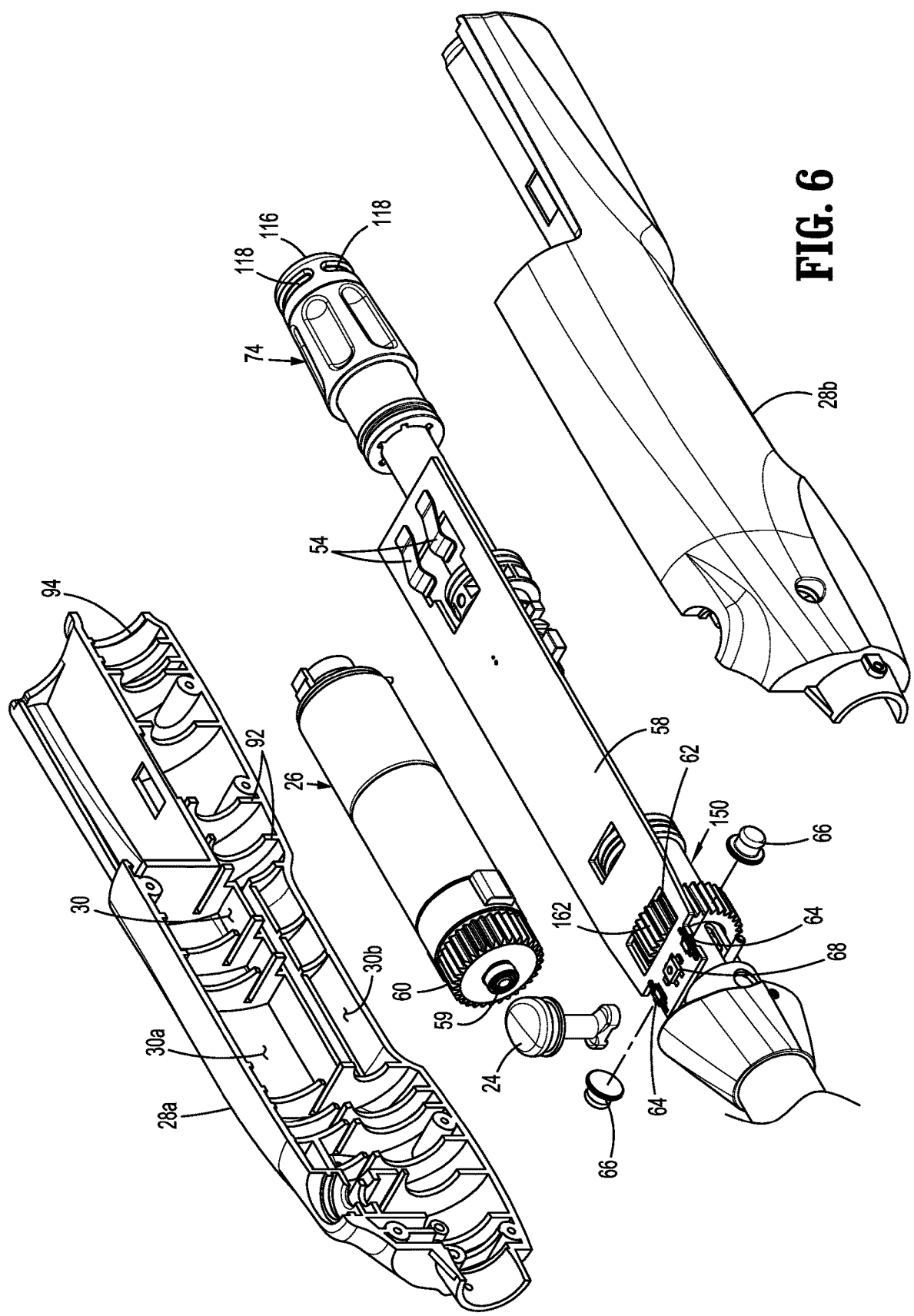
FIG. 6 is an exploded side perspective view of the handle assembly of the stapling device shown in FIG. 1.
Figure 15:
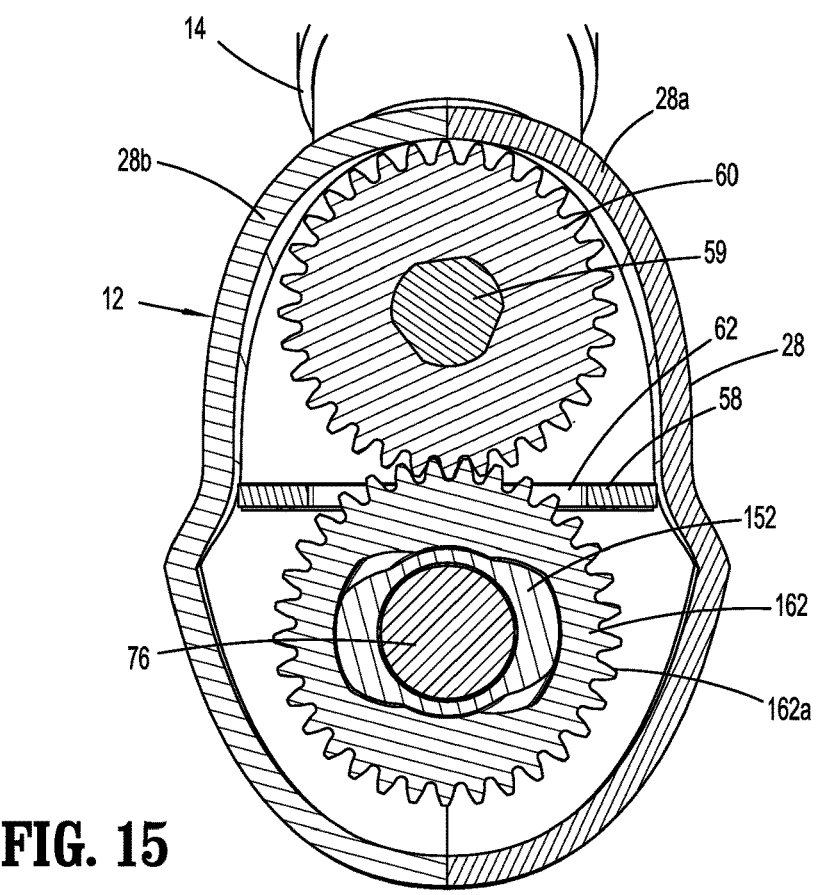
FIG. 15 is a cross-sectional view taken along section line 15-15 of FIG. 5.

FIGS. 4-6 illustrate the internal cavity 30 of the body portion 28 of the handle assembly 12 and the components received in the cavity 30. The handle assembly 12 includes a printed circuit board 58 that divides the internal cavity 30 into an upper half 30a and a lower half 30b as viewed in FIG. 4. The printed circuit board 58 is secured between half-sections 28a, 28b (FIG. 6) of the body portion 28 of the handle assembly 12 and supports the motor 26 within the upper half 30a of the cavity 30 distally of the battery pack 34. The motor 26 includes a rotating drive shaft 59 (FIG. 6) that supports an output gear 60 (FIG. 15) that is aligned with a cutout 62 defined in the printed circuit board 58. Rotation of the drive shaft 59 causes corresponding rotation of the output gear 60.

The printed circuit board 58 includes a distal portion and a proximal portion. The proximal portion of the printed circuit board 58 supports the battery contacts 54 and the distal portion of the 58 supports safety switches 64. The safety switches 64 are positioned to be activated by safety buttons 66 that are positioned on opposite sides of the body portion 28 of the handle assembly 12 as described in further detail below. The distal portion of the 58 also supports a fire switch 68 that is positioned to be activated by the fire button 24. Although not shown, the 58 can also support circuitry to electrically couple the battery pack 34 and motor 26 to the switches 64 and 68 and include a micro controller and motor driver circuitry. The lower half 30b of the cavity 30 receives a proximal portion of an approximation mechanism 72 and a proximal portion of a firing mechanism 73.

Figure 7:
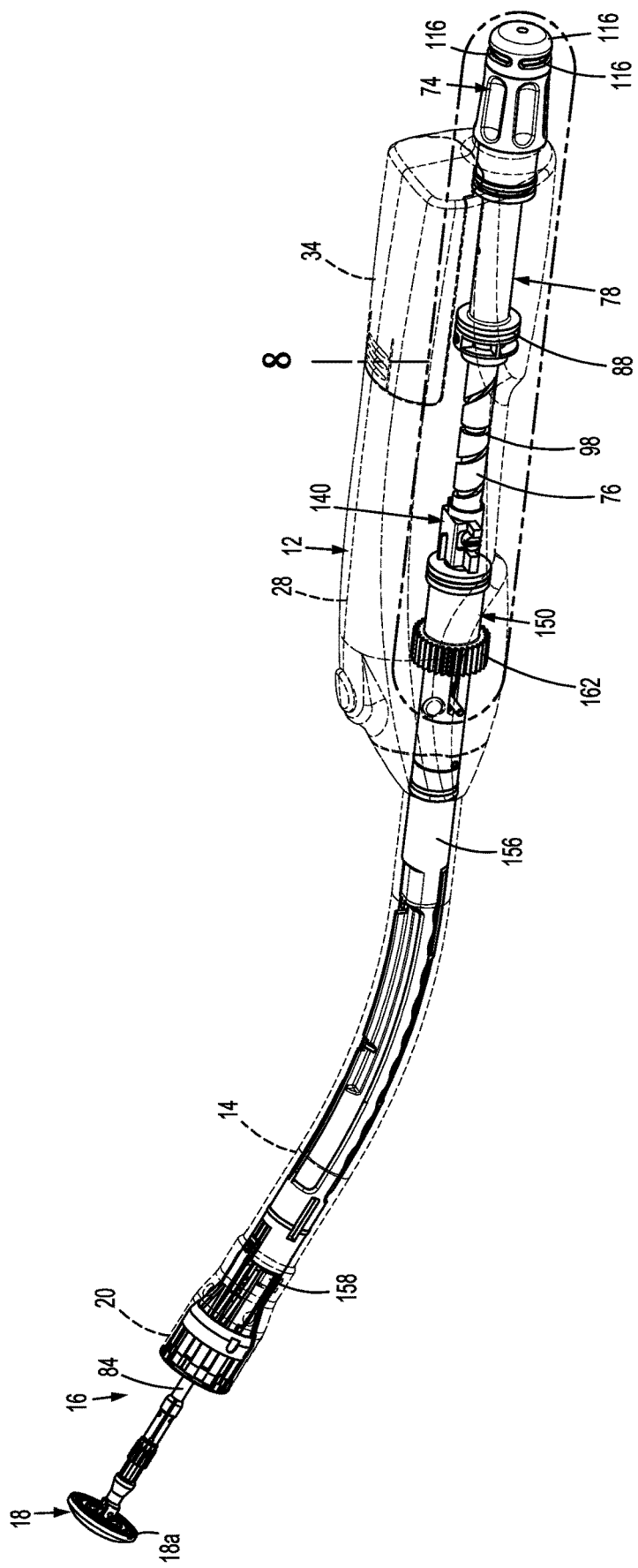
FIG. 7 is a side perspective view of the circular stapling device shown in FIG. 1 in the unclamped position with an outer tube of the adapter assembly and the body of the handle assembly shown in phantom.
Figure 8:
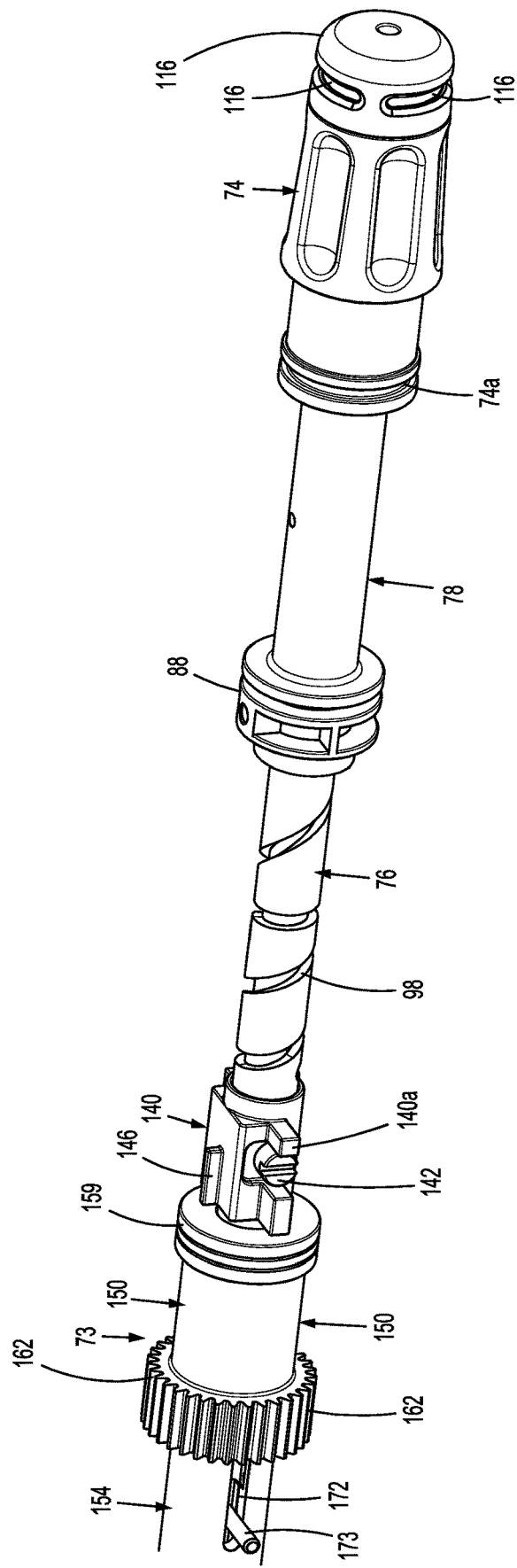
FIG. 8 is an enlarged view of the indicated area of detail shown in FIG. 7.

FIGS. 5-11 illustrate the approximation mechanism 72 which includes the approximation knob 74, a anvil clamp screw 76, a rotatable sleeve 78, first and second screw resilient extensions 80, 82 (FIG. 10), and an anvil retainer trocar 84 (FIG. 7). The rotatable sleeve 78 includes a cylindrical hollow body portion 86 and a cylindrical collar 88 supported on a distal portion of the hollow body portion 86. The rotatable sleeve 78 defines a longitudinal through bore 90. (FIG. 9) The collar 88 has a diameter greater than the body portion 86 and is received between inwardly extending flanges 92 (FIG. 5) formed on inner walls of the half-sections 28a, 28b of the body portion 28 of the handle assembly 12. Receipt of collar 88 between the flanges 92 axially fixes the rotatable sleeve 78 within the body portion 28 of the handle assembly 12 while permitting rotation of rotatable sleeve 78. A proximal portion of the rotatable sleeve 78 extends through an opening 94 (FIG. 6) in the proximal end of the body portion 28 of the handle assembly 12 and is fixedly coupled to the approximation knob 72. The hollow body portion 86 of the rotatable sleeve 78 includes a pair of diametrically opposed ribs 96 (FIG. 9) that are formed on the outer surface of the body portion 76 and are received within slots (not shown) defined within the rotation knob 74 to rotatably fix the rotatable sleeve 78 to the approximation knob 74 such that rotation of the approximation knob 72 causes concurrent rotation of rotatable sleeve 78. In aspects of the disclosure, the distal portion of the approximation knob 74 defines an annular channel 74a that receives an internal rib 75 (FIG. 11) formed on an inner wall of the body portion 28 of the handle assembly 12 to rotatably secure the approximation knob 74 to body portion 28 of the handle assembly 12.

The proximal half of the anvil clamp screw 76 includes a helical channel 98 and is positioned within the through bore 90 of the rotatable sleeve 78. A pin 100 (FIG. 11) is supported on the collar 88 of the rotatable sleeve 78 (FIG. 11) and extends radially from the collar 88 into helical channel 98. Since the rotatable sleeve 78 is axially fixed with respect to body portion 28 of the handle assembly 12, rotation of rotatable sleeve 78 about anvil clamp screw 76 causes pin 100 (FIG. 11) to move along helical channel 98 of anvil clamp screw 76 to effect axial movement of anvil clamp screw 76 within the body portion 28 of the handle assembly 12.

Figure 9:
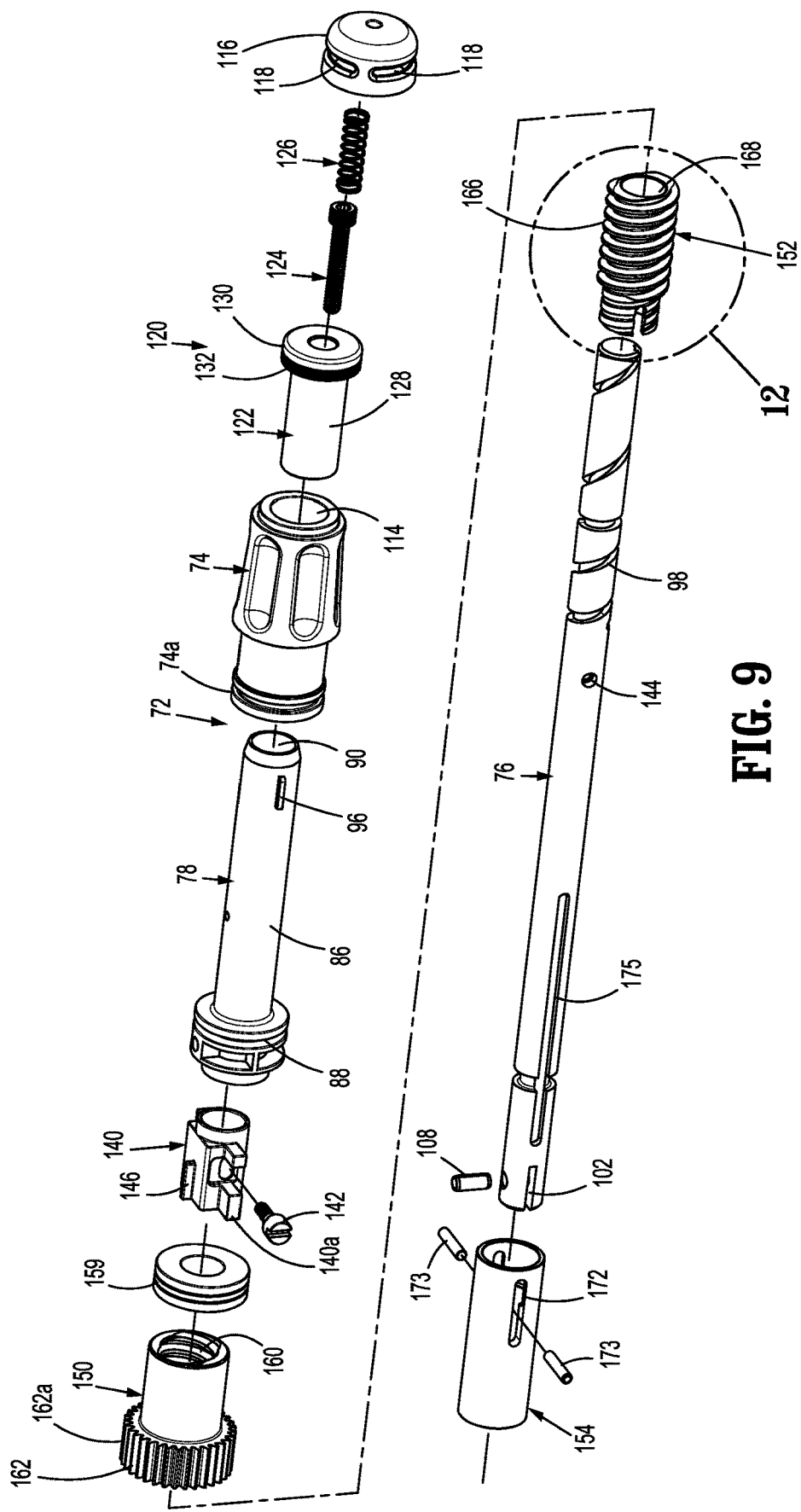
FIG. 9 is an exploded side perspective view of approximation and firing mechanisms of the handle assembly shown in FIG. 1.
Figure 10:
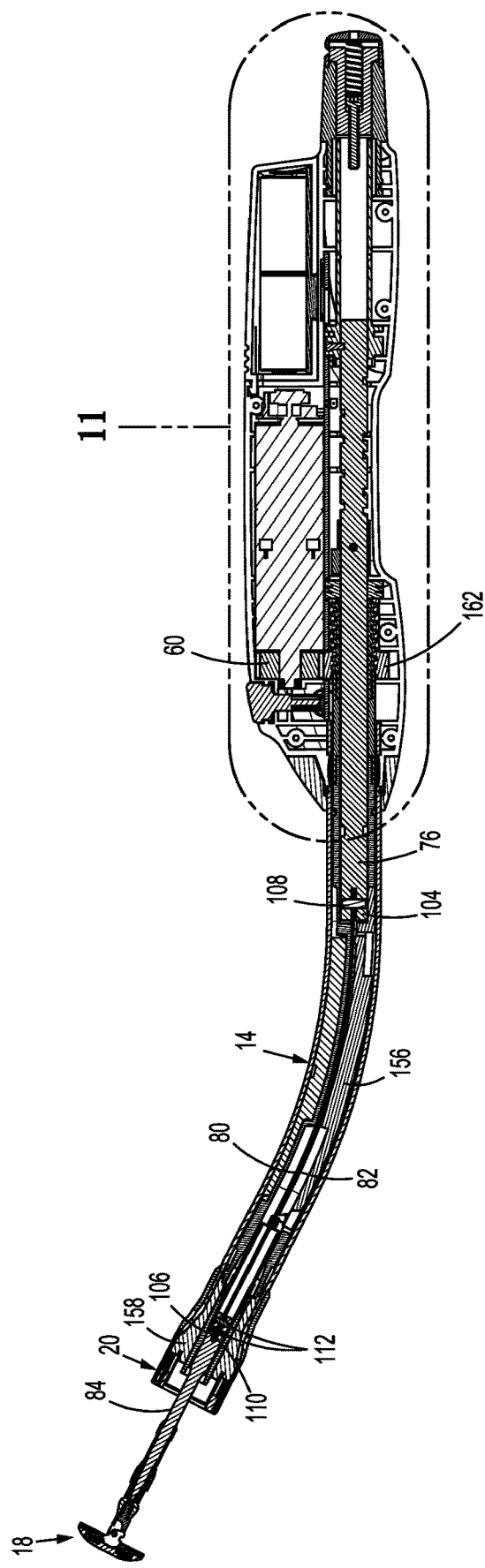
FIG. 10 is a cross-sectional view taken along a longitudinal axis of the circular stapling device shown in FIG. 1 in the unclamped position.
Figure 11:
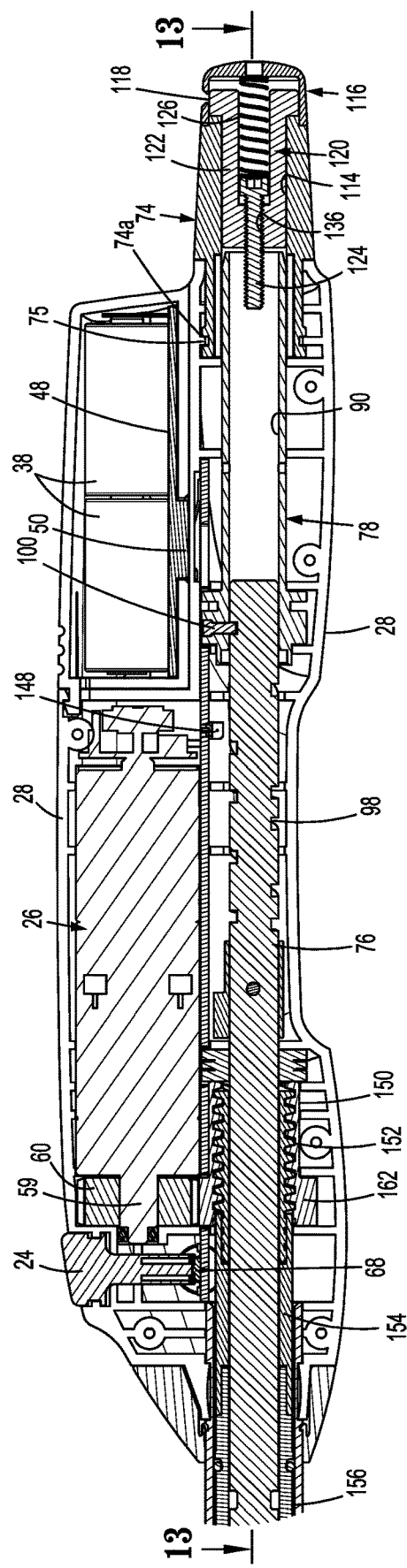
FIG. 11 is an enlarged view of the indicated area of detail shown in FIG. 10.
Figure 12:
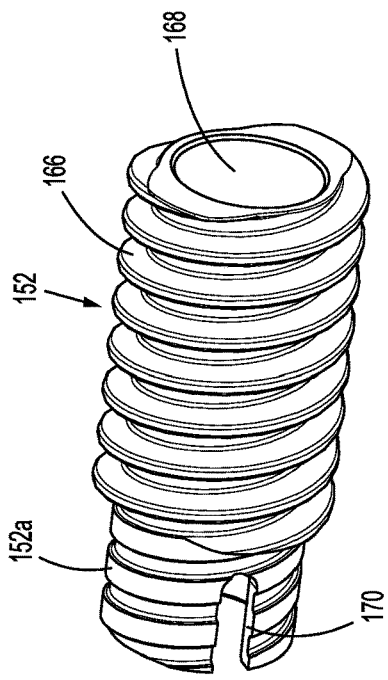
FIG. 12 is an enlarged view of the indicated area of detail shown in FIG. 9.
Figure 13:
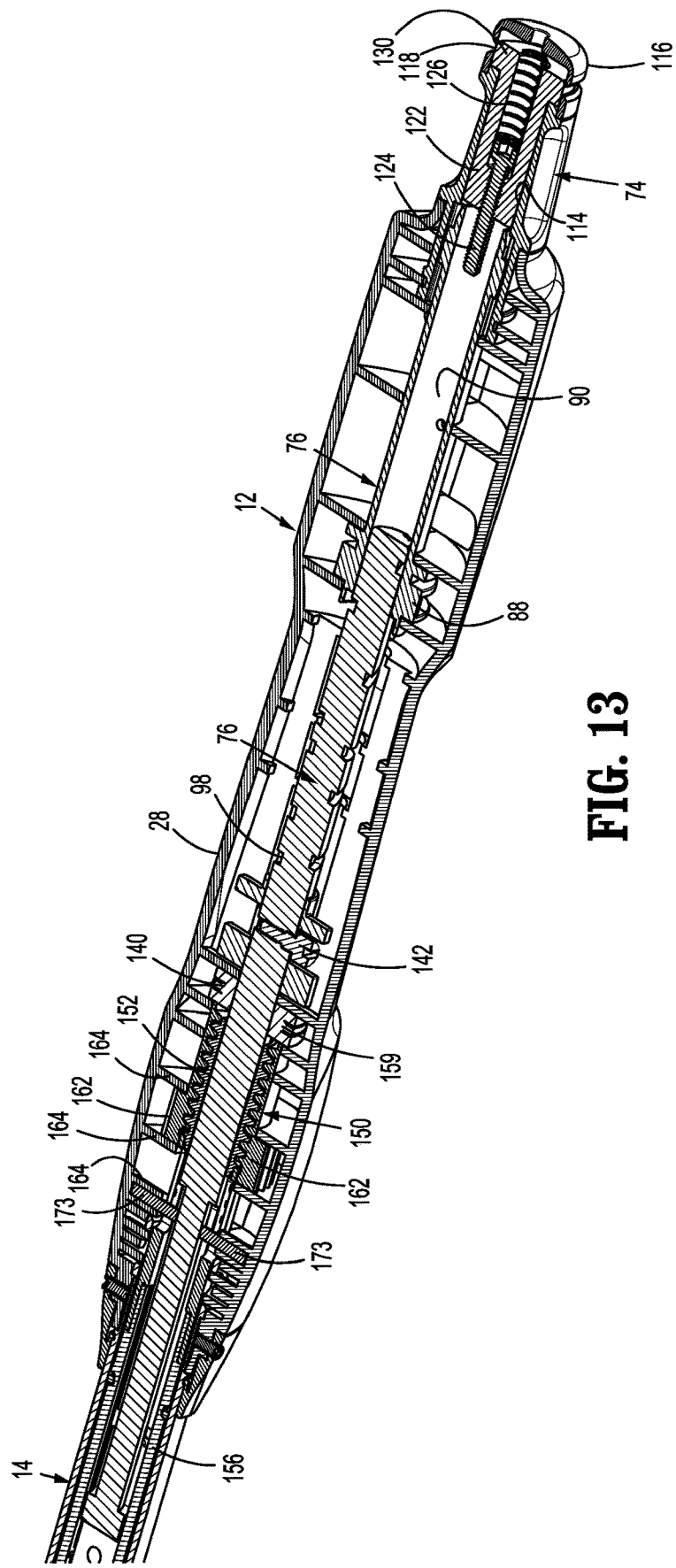
FIG. 13 is a cross-sectional view taken along section line 11-11 of FIG. 12.

The anvil clamp screw 76 has a distal portion that defines a transverse slot 102 (FIG. 9). The screw extensions 80, 82 each include a proximally located flexible flat band portion 104 (FIG. 10) and a distally located flat band portion 106. The band portions 104 are secured within the transverse slot 102 of the drive screw 76 with a pin 108 (FIG. 9) to secure the band portions 80, 82 to the drive screw 76. The band portions 80, 82 extend from the drive screw 76 through the elongated body 14 (FIG. 10) into the shell assembly 20. The flat band portions 106 of the screw extensions 80, 82 are secured within a slot 110 (FIG. 10) defined in the anvil retainer 84 with pins 112 (FIG. 10) to secure the anvil retainer 84 to the screw extensions 80, 82. When the approximation knob 74 is rotated to move the anvil clamp screw 76 axially within the body portion 28 of the handle assembly 12, the screw extensions 80, 82 are also moved axially within the elongate body 14 and the anvil retainer 84 is moved axially within the shell assembly 20 (FIG. 10). It is envisioned that although pins are shown to secure the screw extensions 80, 82 to the drive screw 76 and the anvil retainer 84 (FIG. 10), other techniques and/or attachment devices can be used to perform this function.

The anvil retainer 84 is configured to be releasably coupled to the anvil assembly 18 (FIG. 10) such that rotation of the approximation knob 74 moves the anvil assembly 18 in relation to the shell assembly 20 between the open and clamped positions. U.S. Pat. No. 7,303,106 describes a stapling device including an anvil assembly and anvil retainer that are releasably coupled together and are suitable for use with the stapling device 10.

The approximation knob 74 defines a through bore 114 and supports an indicator cap 116. The indicator cap 116 is fixedly secured to a proximal portion of the approximation knob 74 and defines windows 118 that are spaced about the indicator cap 116. The approximation knob 74 supports an indicator assembly 120 (FIG. 9) that includes an indicator 122, an adjustment member or screw 124, and a biasing member 126. The indicator 122 includes a cylindrical body 128 and a head portion 130 that has a diameter that is larger than the cylindrical body 128. The head portion 130 of the indicator 122 is received within the indicator cap 116 and includes indicia 132 (FIG. 9). The indicator 122 is movable within the approximation knob 74 from an advanced position towards a retracted position in response to movement of the drive screw 76 towards a retracted position to move the head portion 130 of the indicator 122 within the indicator cap 116 from an advanced position to a retracted position. The indicia 132 is visible through the windows 118 in the indicator cap 116 when the stapling device 10 is moved to a clamped position. As used herein, the term "clamped position" means positions in which the anvil assembly 18 located in close enough approximation with the staple cartridge 20a (FIG. 1) of the shell assembly 20 such that staples can be properly formed against the anvil assembly 18. As such, the clamped position includes a range of positions. The clamped position is determined by the thickness of tissue being clamped and the discretion of a clinician.

The adjustment screw 124 is threaded into a threaded bore 136 defined in the distal portion of the indicator 122 to secure the adjustment screw 124 to the indicator 122. The adjustment screw 124 extends into the through bore 90 of the rotatable sleeve 78 and includes a distal end that is positioned to engage the drive screw 76 when the drive screw 76 is moved towards the retracted position. The biasing member 126 is positioned between the indicator cap 116 and the indicator 122 to urge the indicator 122 towards the advanced position. When the drive screw 76 moves towards its' retracted position (FIG. 20), the drive screw 76 engages the adjustment screw 124 to move the adjustment screw 124 and the indicator 122 proximally within the approximation knob 74. As the indicator 122 moves within the approximation knob 74, the head portion 130 of the indicator 122 moves within the indicator cap 116 such that the indicia 132 becomes visible through the windows 118 in the indicator cap 116. This provides an indication to a clinician that the stapling device 10 (FIG. 1) is in a fire-ready position, i.e., that the anvil assembly 18 and the shell assembly 20 are in close enough opposition to facilitate proper formation of staples. The position of the adjustment screw 124 within the through bore 90 of the rotatable sleeve 78 can be adjusted or calibrated by rotating the adjustment screw 124 during manufacturing of the stapling device 10 (FIG. 1) to properly position the adjustment screw 124 within the through bore 90 of the rotatable sleeve 78 so that the indicia 132 moves into the windows 118 of the indicator cap 116 when the anvil assembly 18 and the shell assembly 20 are properly spaced from each other.

The drive screw 76 supports a carriage 140 (FIG. 9) that is secured to the drive screw 76 with a carriage screw 142. The carriage 140 is received in a threaded bore 144 in the drive screw 76 and is movable with the drive screw 76 as the drive screw 76 moves within the body portion 28 of the handle assembly 12 between retracted and advanced positions. The carriage 140 includes an elongate rib 146 (FIG. 9) that engages or activates a switch, e.g., a photo interrupter 148 (FIG. 17), supported within the handle assembly 12 when the stapling device 10 (FIG. 1) is moved to the clamped position to activate the safety switches as described below. The carriage 140 also includes wings 140a (FIG. 16) that are received in slots 141 defined within the body portion 28 of the handle assembly 12 to prevent rotation of the carriage 140 and guide the carriage 140 within the body portion 28 of the handle assembly 12 of the stapling device 10.

FIGS. 5-13 illustrate the firing mechanism 73 (FIG. 8) which includes a fire gear 150, a fire screw 152, an extender 154, a pusher link 156 (FIG. 10), and a pusher 158 (FIG. 10). The fire gear 150 is rotatably supported about the drive screw 76 and defines an internal threaded bore 160 and an outer gear member 162 that includes a plurality of gear teeth 162a. The gear member 162 is received between flanges 164 (FIG. 13) formed on the body portion 28 of the handle assembly 12 such that the fire gear 150 can rotate within the body portion 28 of the handle assembly 12 but is axially fixed. The fire screw 152 is received within the internal threaded bore 160 of the fire gear 150 and includes an outer threaded portion 166 and an inner through bore 168. The drive screw 76 extends through the through bore 168 of the fire screw 152 such that the fire screw 152 is slidable about the drive screw 76.

Figure 14:
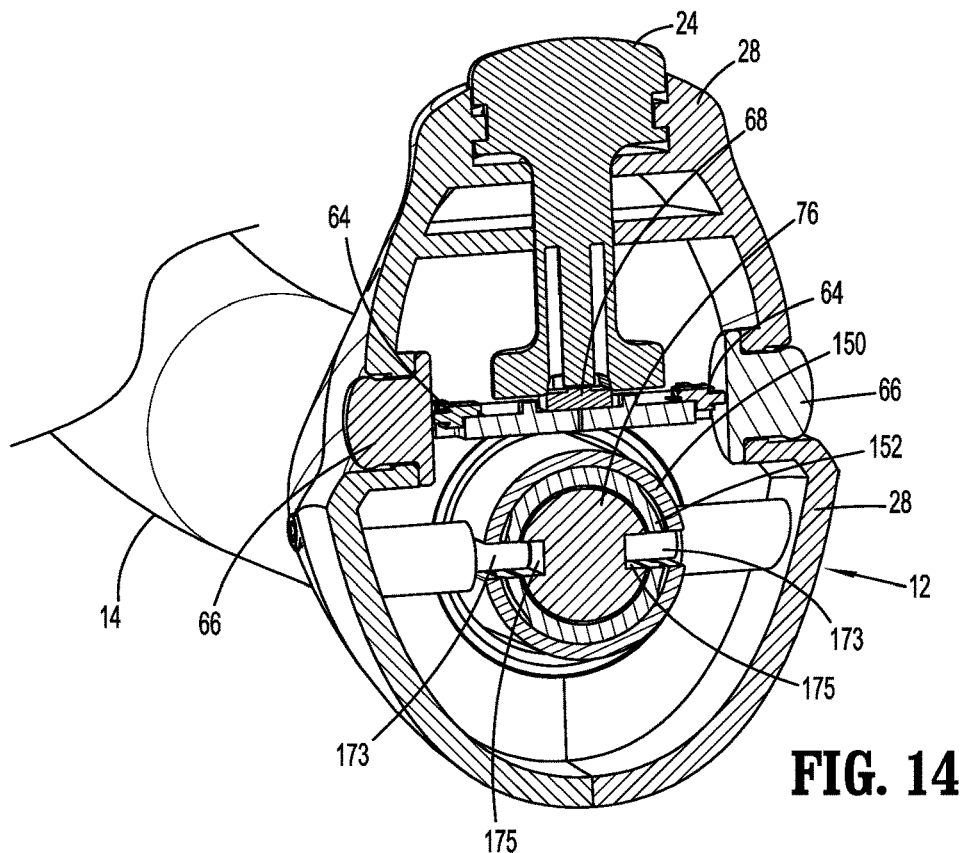
FIG. 14 is a cross-sectional view taken along section line 14-14 of FIG. 5.

The fire screw 152 includes a distal portion 152a that has a reduced diameter and is received within a proximal portion of the extender 154. The distal portion 152a of the fire screw 152 includes diametrically opposed longitudinal slots 170 that are aligned with longitudinal slots 172 formed within the extender 154. Pins 173 (FIG. 14) are supported on the body portion 28 and extend through the slots 170 and 172 and into channels 175 (FIG. 9) formed in the body portion 28 of the handle assembly 12 to prevent rotation of the extender 154 in relation to the fire screw 152. The distal portion of the extender 154 receives a proximal portion of the pusher link 156 and the distal portion of the pusher link 156 is engaged with the pusher 158 which is received within the shell assembly 20 (FIG. 10). In aspects of the disclosure, a thrust bearing 159 (FIG. 23) is supported within the body portion 28 of the handle assembly 12 and is engaged with the proximal end of the fire gear 150 to absorb the firing forces generated by the fire gear 150.

When the motor 26 is activated, the output gear 60 of the motor 26 is rotated. The output gear 60 is engaged with outer gear member 162 (FIG. 15) of the fire gear 150 such that rotation of the output gear 60 rotates the fire gear 150. The internal threaded bore 160 of the fire gear 150 is threadedly engaged with the outer threaded portion 166 of the fire screw 152. As the fire gear 150 is rotated, the fire screw 152 is driven longitudinally within the fire gear 150 about the drive screw 76. The distal portion 152a of the fire screw 152 is engaged with the proximal portion of the extender 154 and the distal portion of the extender 154 is engaged with the proximal portion of the pusher link 156 such that advancement of the fire screw 152 advances the pusher link 156 within the elongate body 14 of the stapling device 10 (FIG. 10). The distal portion of the pusher link 156 is coupled to the pusher 158 such that advancement of the pusher link 156 causes the pusher 158 (FIG. 10) to move within the shell assembly 20 to eject staples from the shell assembly 20.

FIG. 6 illustrates the safety buttons 64, the safety switches 66, the fire button 24, and the fire switch 68. When the approximation knob 74 is manually actuated to move the stapling device 10 (FIG. 1) to the clamped position in the fire-ready zone, the elongated rib 146 on the carriage 140 will move into the photo interrupter 148 (FIG. 5) to interrupt a light beam. When this occurs, the photo interrupter 148, which is connected by circuitry within the handle assembly 12 to the safety switches 66, will cause the safety buttons 64 to illuminate to provide an indication to a clinician that the stapling device 10 is able to be fired. The safety buttons 64 can include an LED or other illuminating device to illuminate the safety buttons 64. To fire the stapling device 10, one of the safety buttons 64 must be pressed to close the safety switches 66 and activate the fire switch 68. Once one of the safety buttons 64 is pressed, the fire button 24 can be pressed to close the fire switch 68 and initiate firing of the stapling device 10, i.e., activate the motor 26 to advance the pusher link 156 and advance the pusher 158 to fire staples from the shell assembly 20. The fire button 24 may also be illuminated such as a with a light emitting diode (LED). For example, when the safety buttons 64 are pressed, the fire button 24 will illuminate to provide an indication to a clinician that the stapling device 10 is ready to be fired. It is noted that the safety switches 66 will not activate the firing switch 68 until the elongated rib 146 on the carriage 140 moves into the photo interrupter 148.

In aspects of the disclosure, the safety buttons 64 and the fire button 24 may be configured to blink when the stapling device 10 is coupled to the battery pack 34 prior to movement of the stapling device 10 to the clamped position. In this aspect of the disclosure, the safety buttons 64 will blink until the stapling device is moved to the clamped position. When the stapling device 10 is moved to the clamped position, the safety buttons 64 will illuminate continuously but the fire button 24 will continue to blink intermittently until one of the safety buttons 64 is depressed. When one of the safety buttons 64 is depressed to close the safety switch 66, the fire button 24 will illuminate continuously to indicate to a clinician that the stapling device 10 is ready to fire. In aspects of the disclosure, the circuitry within the stapling device 10 includes a timer that resets the safety switches 66 if the stapling device 10 is not fired within a predetermined time after one of the safety buttons 64 is depressed. If the stapling device 10 is not fired in the predetermined time, the safety switches 66 will reset such that one of the safety buttons 64 will have to be depressed again to activate the fire button 24. In aspects of the disclosure, the predetermined time can be from about 10 seconds to about 30 seconds although other times are envisioned.

Figure 20:
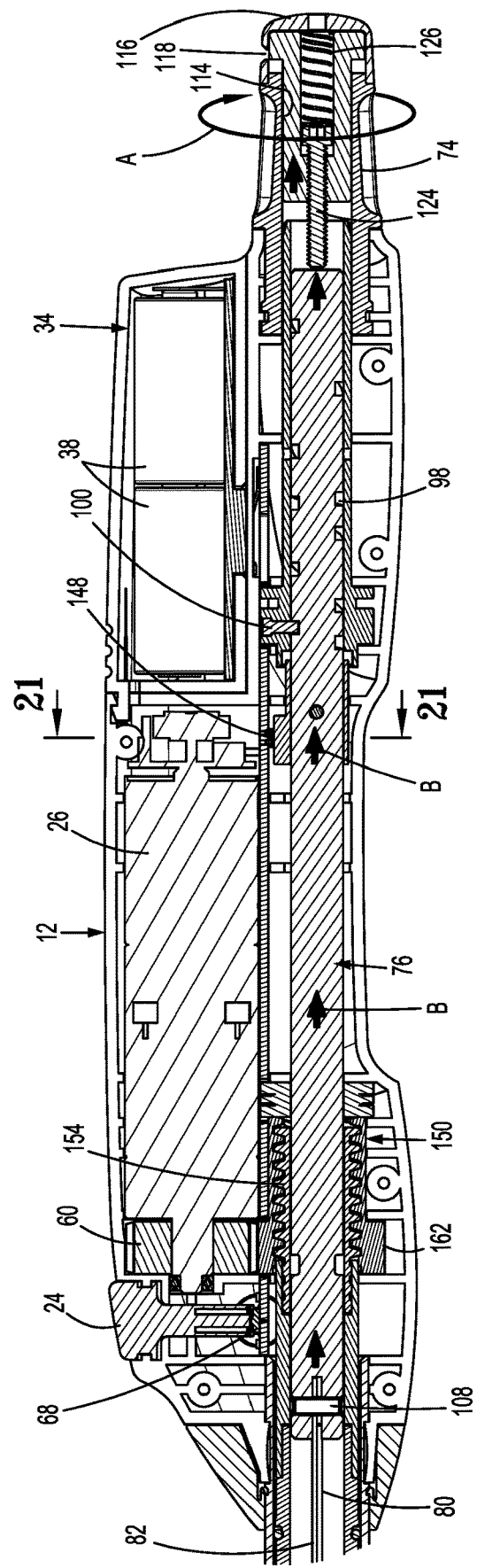
FIG. 20 is an enlarged view of the indicated area of detail shown in FIG. 19.
Figure 21:
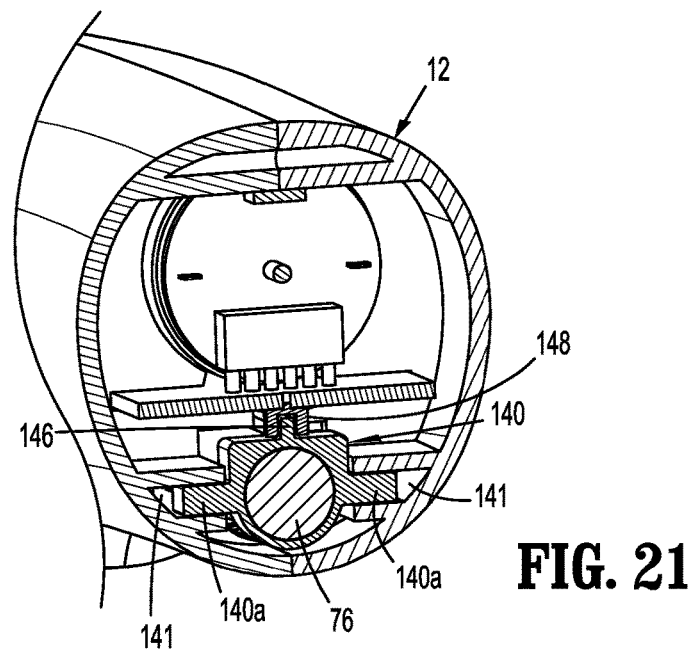
FIG. 21 is a cross-sectional view taken along section line 21-21 of FIG. 20.

FIGS. 19-21 illustrate the stapling device 10 as the stapling device 10 is moved from the open position to the clamped position. When the approximation knob 74 is rotated in the direction indicated by arrow "A" in FIG. 20, the drive screw 76 is retracted in the direction of arrow "B". As summarized above, the drive screw 76 is coupled to the screw extensions 80, 82 and the screw extensions 80, 82 are coupled to the anvil retainer 84 such that movement of the drive shaft 76 in the direction of arrow "B" moves the anvil retainer in the direction of arrow "C" in FIG. 19 to move the anvil assembly 18 in the direction of arrow "D" to the clamped and fire-ready position (FIG. 19). As shown in FIG.

21, when the drive screw 76 is retracted and the stapling device 10 moves to the clamped position, the elongate rib 146 on the carriage 140 moves into the photo interrupter 148 to activate the safety switches 66. When this occurs, the safety switches 66 will illuminate to provide an indication to a clinician that the stapling device 10 is ready to be fired. In this position, one of the safety buttons 64 can be depressed to activate the fire button 24. When one of the safety buttons 64 is depressed, the fire button 24 will illuminate.

Figure 22:
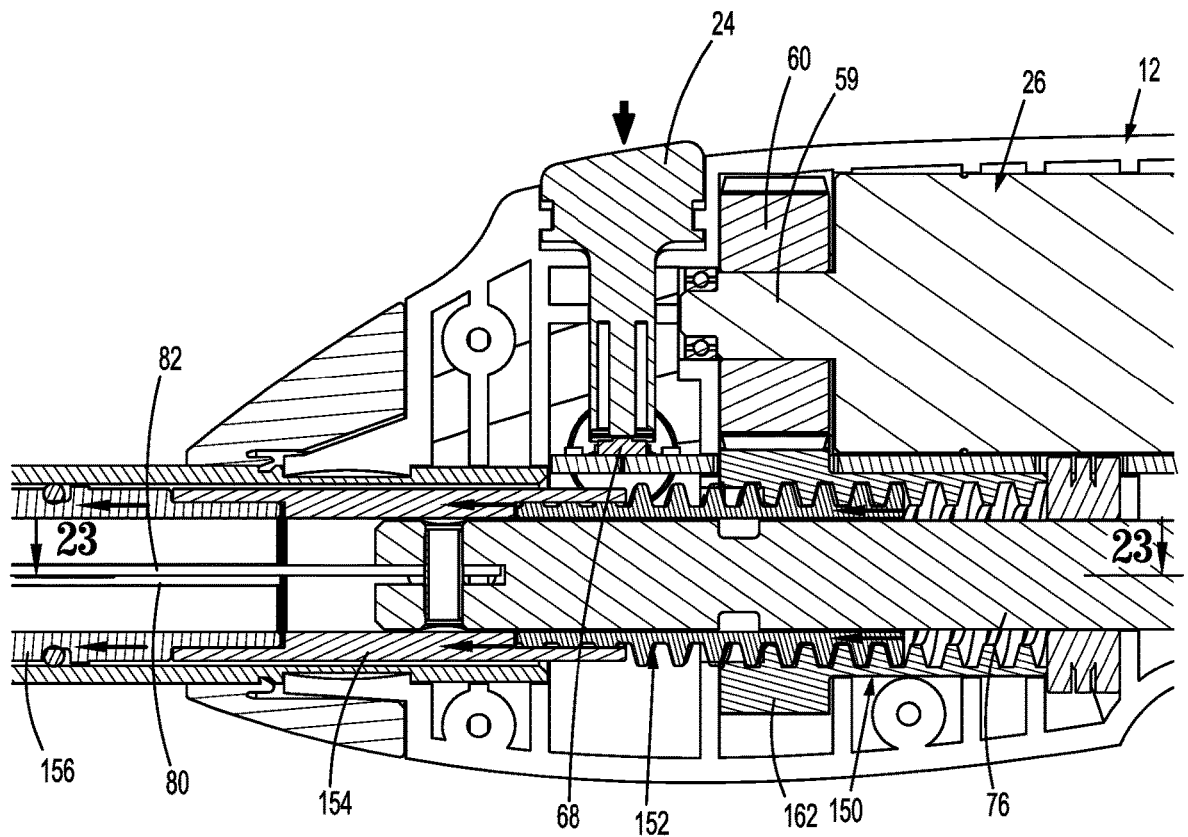
FIG. 22 is a side cross-sectional view taken through a distal portion of the handle assembly as the circular stapling device is being fired.
Figure 23:
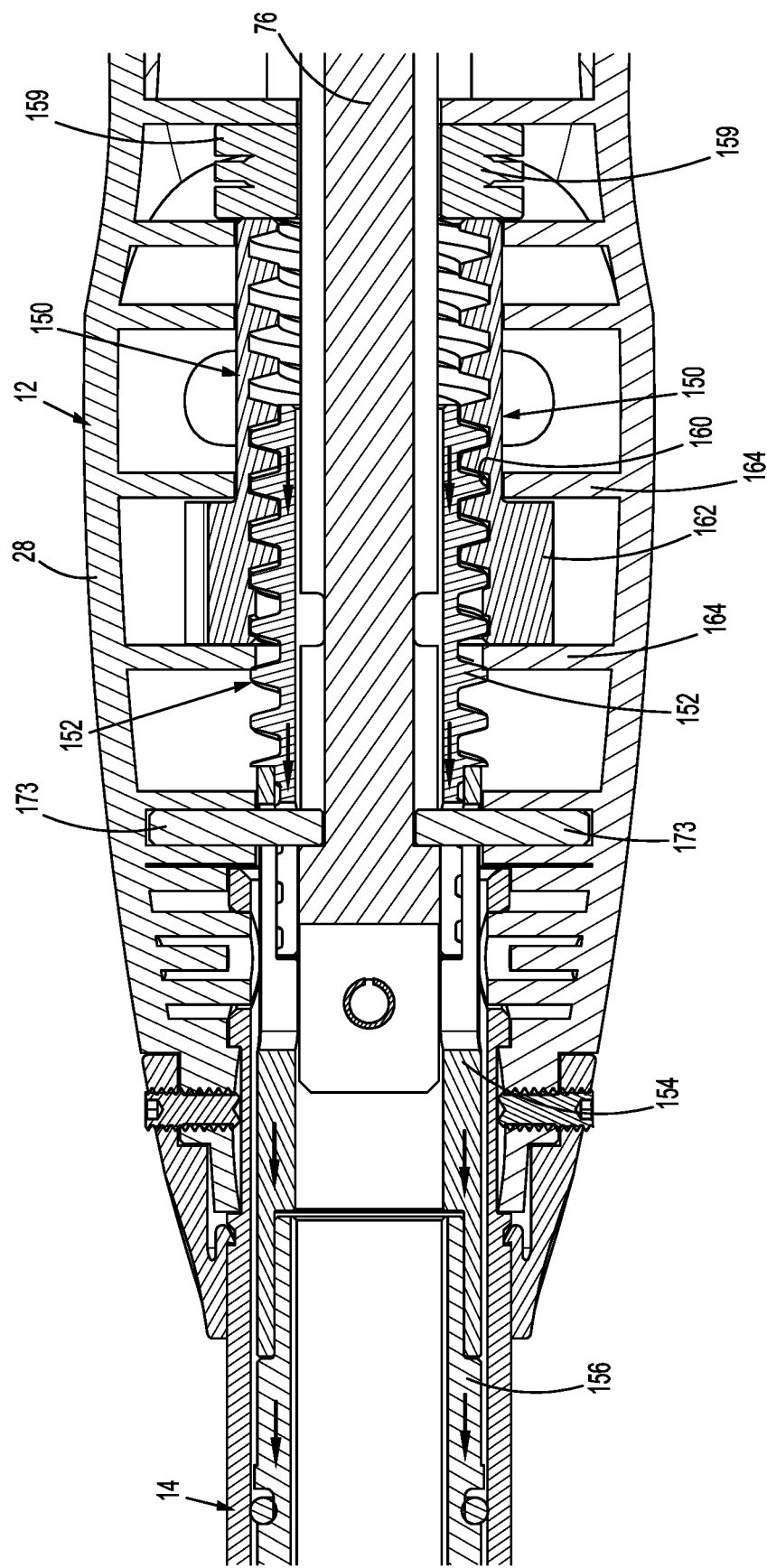
FIG. 23 is a cross-sectional view taken along section line 23-23 of FIG. 22.

FIGS. 22 and 23 illustrate the stapling device 10 as the stapling device 10 is fired. When the firing button 24 is depressed to activate the firing switch 68, the motor is activated to rotate the output gear 60. When the output gear 60 is rotated, the output gear 60 rotates the fire gear 150. The internal threaded bore 160 of the fire gear 150 is threadedly engaged with the outer threaded portion 166 of the fire screw 152. As the fire gear 150 is rotated, the fire screw 152 is driven longitudinally within the fire gear 150 about the drive screw 76. The distal portion 152 of the fire screw 152 is engaged with the proximal portion of the extender 154 and the distal portion of the extender 154 is engaged with the proximal portion of the pusher link 156 such that advancement of the fire screw 152 advances the pusher link 156 within the elongate body 14 of the stapling device 10 (FIG. 10). The distal portion of the pusher link 156 is coupled to the pusher 158 such that advancement of the pusher link 156 causes the pusher 158 (FIG. 10) to move within the shell assembly 20 to eject staples from the shell assembly 20. The disclosed stapling device 10 incorporates benefits of manually operated stapling devices and powered stapling devices into a single instrument that can be manufactured as a disposable instrument. More particularly, the stapling device 10 includes a manually operated approximation mechanism 72 that preserves tactile feedback to the clinician for user-controlled compression. In addition, the stapling device 10 includes a powered or motorized firing mechanism 73 that allows for controlled stable firing with minimal influence on tissue movement.

Persons skilled in the art will understand that the devices and methods specifically described herein and illustrated in the accompanying drawings are non-limiting exemplary embodiments. It is envisioned that the elements and features illustrated or described in connection with one exemplary embodiment may be combined with the elements and features of another without departing from the scope of the disclosure. As well, one skilled in the art will appreciate further features and advantages of the disclosure based on the above-described embodiments. Accordingly, the disclosure is not to be limited by what has been particularly shown and described, except as indicated by the appended claims.

What is claimed is:

1. A surgical stapling device comprising:
an elongate body having a distal portion and a proximal portion;
an anvil retainer extending from the distal portion of the elongate body;
a tool assembly supported on the distal portion of the elongate body, the tool assembly including an anvil assembly having an annular staple forming surface and a shell assembly having an annular staple cartridge, the anvil assembly coupled to the anvil retainer and being movable with the anvil retainer to move the tool assembly between an open position in which the annular staple forming surface of the anvil assembly is spaced from the annular staple cartridge of the shell assembly and a clamped position in which annular staple forming surface of the anvil assembly is in juxtaposed opposition to the annular staple cartridge of the shell assembly, the shell assembly further including a staple pusher and an annular knife that are movable in relation to the annular staple cartridge between retracted and advanced positions to eject staples from the annular staple cartridge and cut tissue; and
a handle assembly including a body portion, a manually operated approximation mechanism including a drive screw, and a motorized firing mechanism, the approximation mechanism coupled to the anvil retainer and manually operable to retract the anvil retainer into the shell assembly to move the tool assembly from the open position to the clamped position, the firing mechanism including a fire screw positioned about the drive screw and a motor that is activated to advance the fire screw longitudinally about the drive screw to move the staple pusher and the annular knife between their retracted and advanced positions, wherein the drive screw and the fire screw define axes that are coaxial.

2. The surgical stapling device of claim 1, wherein the body portion of the handle assembly supports a battery pack, the battery pack including one or more batteries that are electrically coupled to the motor by circuitry.

3. The surgical stapling device of claim 1, wherein the manually operated approximation mechanism further includes a rotation knob, a rotatable sleeve, and a screw extension, the rotatable knob coupled to the drive screw by the rotatable sleeve such that rotation of the rotation knob causes longitudinal movement of the drive screw between advanced and retracted positions.

4. The surgical stapling device of claim 3, wherein the drive screw is coupled to the anvil retainer by one or more extensions, the one or more extensions being formed of a resilient material and extending through the elongate body.

5. The surgical stapling device of claim 3, wherein the handle assembly supports a photo interrupter, and the drive screw supports a carriage having an elongate rib, the carriage being fixedly secured to the drive screw and movable with the drive screw between advanced and retracted positions, wherein the elongate rib is received within the photo interrupter when the carriage and the drive screw near their retracted positions.

6. The surgical stapling device of claim 5, wherein the handle assembly includes at least one safety switch supported within the body portion of the handle assembly and at least one safety button supported on the body portion of the handle assembly, the at least one safety switch being activated when the elongate rib of the carriage is received within the photo interrupter.

7. The surgical stapling device of claim 6, wherein the handle assembly includes a fire switch and a fire button, the fire switch supported within the body portion of the handle assembly and the fire button supported on the body portion of the handle assembly, the fire switch being activated when the at least one safety button is depressed to close the at least one safety switch after the safety switch is activated, the fire button being depressible to close the fire switch after the fire switch is activated to activate the motor.

8. The surgical stapling device of claim 7, wherein the at least one safety switch includes first and second safety switches and the at least one safety button includes first and second safety buttons, the first and second safety buttons supported on opposite sides of the body portion of the handle assembly.

9. The surgical stapling device of claim 7, wherein the safety button illuminates when the safety switch is activated, and the fire button illuminates when the fire switch is activated.

10. The surgical stapling device of claim 3, wherein the approximation knob defines a through bore and has a proximal portion that supports an indicator cap, the indicator cap defining at least one window.

11. The surgical stapling device of claim 10, further including an indicator mechanism, the indicator mechanism including an indicator, an adjustment member, and a biasing member, the indicator including indicia and being movable within the through bore of the approximation knob from an advanced position to a retracted position in response to movement of the drive screw from its advanced position towards its retracted position to position the indicia in a position within the approximation knob to be visualized through the at least one window in the indicator cap.

12. The surgical stapling device of claim 11, wherein the adjustment member is threadedly engaged with the indicator and includes a distal portion that extends distally of the indicator and is positioned to engage the drive screw as the drive screw is moved towards its['] retracted position to move the indicator towards its retracted position.

13. The surgical stapling device of claim 12, wherein a longitudinal position of the adjustment member in relation to the indicator is adjustable to properly position the adjustment member in relation to the drive screw within the through bore of the approximation knob so that the indicia moves into the at least one window of the indicator cap when the tool assembly is in the clamped position.

14. The surgical stapling device of claim 1, wherein the motorized firing mechanism further includes a fire gear, an extender, a pusher link, and a pusher, and the motor includes a drive shaft that supports an output gear, the fire gear including an outer gear member that is engaged with the output gear such that activation of the motor causes rotation of the fire gear.

15. The surgical stapling device of claim 14, wherein fire gear defines an internally threaded bore and the fire screw includes an outer threaded portion, the fire screw received within the internally threaded bore of the of the fire gear such that rotation of the fire gear causes longitudinal movement of the fire screw between retracted and advanced positions.

16. The surgical stapling device of claim 15, wherein the fire screw is coupled to the pusher link by the extender and the pusher link is coupled to the pusher such that longitudinal movement of the fire screw causes corresponding longitudinal movement of the pusher link and the pusher.

17. A handle assembly comprising:
a body portion, a manually operated approximation mechanism, and a motorized firing mechanism, the approximation mechanism including an approximation knob and a drive screw defining a first longitudinal axis, the approximation knob being rotatable to cause longitudinal movement of the drive screw, the firing mechanism including a motor and a fire screw defining a second longitudinal axis, the fire screw positioned about the drive screw such that the first and second longitudinal axes are coaxial, the motor being coupled to the fire screw such that activation of the motor causes longitudinal movement of the fire screw.

18. The handle assembly of claim 17, wherein the motorized firing mechanism further includes a fire gear, and the motor includes an output shaft that supports an output gear, the fire gear including an outer gear member that is engaged with the output gear such that activation of the motor causes rotation of the fire gear.

19. The handle assembly of claim 18, wherein fire gear defines an internally threaded bore and the fire screw includes an outer threaded portion, the fire screw being received within the internally threaded bore of the fire gear such that rotation of the fire gear causes longitudinal movement of the fire screw between retracted and advanced positions.

20. An approximation knob assembly comprising:
an approximation knob defining a through bore and having a proximal portion;
an indicator cap supported on the proximal portion of the approximation knob, the indicator cap defining at least one window; and
an indicator mechanism including an indicator, an adjustment member, and a biasing member, the indicator including indicia and being movable within the through bore of the approximation knob from an advanced position to a retracted position to position the indicia in a location within the approximation knob to be visualized through the at least one window in the indicator cap, the adjustment member being threadedly engaged with the indicator and including a distal portion that extends distally from the indicator, wherein a longitudinal position of the adjustment member is adjustable in relation to the indicator.

* * * * *